(12) United States Patent
Rammo et al.

(10) Patent No.: US 11,433,173 B2
(45) Date of Patent: Sep. 6, 2022

(54) SYSTEM FOR EXTRACORPOREAL BLOOD TREATMENT, TREATMENT APPARATUS, KIT AND METHOD FOR OPERATING A SYSTEM FOR EXTRACORPOREAL BLOOD TREATMENT

(71) Applicant: FRESENIUS MEDICAL CARE DEUTSCHLAND GMBH, Bad Homburg (DE)

(72) Inventors: Jorg Rammo, Spiesen-Elversberg (DE); Jurgen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/468,299

(22) PCT Filed: Dec. 14, 2017

(86) PCT No.: PCT/EP2017/082781
§ 371 (c)(1),
(2) Date: Jun. 11, 2019

(87) PCT Pub. No.: WO2018/109070
PCT Pub. Date: Jun. 21, 2018

(65) Prior Publication Data
US 2020/0069860 A1 Mar. 5, 2020

(30) Foreign Application Priority Data

Dec. 15, 2016 (DE) ...................... 10 2016 014 892.6
Jun. 16, 2017 (DE) ...................... 10 2017 210 134.2

(51) Int. Cl.
*A61M 1/34* (2006.01)
*A61M 1/26* (2006.01)
(Continued)

(52) U.S. Cl.
CPC ............ *A61M 1/3413* (2013.01); *A61M 1/16* (2013.01); *A61M 1/1698* (2013.01);
(Continued)

(58) Field of Classification Search
CPC ...... A61M 1/16; A61M 1/1698; A61M 1/267; A61M 1/3334; A61M 1/34; A61M 1/3413;
(Continued)

(56) References Cited

U.S. PATENT DOCUMENTS 4,770,774 A    9/1988 Ida et al.
2003/0012941 A1    1/2003 Fujita et al.
(Continued)

FOREIGN PATENT DOCUMENTS

CN    201320317 Y    10/2009
CN    102500003 A    6/2012
(Continued)

OTHER PUBLICATIONS

Office Action issued in corresponding Chinese Patent Application No. 201780078055.6 dated Jun. 23, 2021 (English translation only) (10 pages).
(Continued)

*Primary Examiner* — John Kim
(74) *Attorney, Agent, or Firm* — Kilyk & Bowersox, P.L.L.C.

(57) ABSTRACT

The present invention relates to a system (100) for extracorporeal blood treatment comprising a first inlet (1) for introducing a bloodstream to be treated into the system (100), three blood treatment apparatus (A, D, G), as well as an outlet (2) for discharging a treated bloodstream from the system (100), wherein the system comprises an adsorber apparatus (A) and/or a plasma separator apparatus, a dialysis apparatus (D) and a gas exchange apparatus (G), and
(Continued)

wherein the three blood treatment apparatus (A, D, G) are sequentially connected in series in a functional state of system (100) application between the inlet (1) and the outlet (2) of the system relative to a direction of blood flow of a bloodstream to be treated and can be consecutively perfused extracorporeally by a bloodstream to be treated. The present invention further relates to a treatment apparatus comprising such a system, a kit comprising the components of such a system, a method for operating such a system (100) as well as a method for extracorporeal blood treatment with such a system (100).

21 Claims, 5 Drawing Sheets

(51) Int. Cl.
   *A61M 1/16* (2006.01)
   *A61M 1/36* (2006.01)
(52) U.S. Cl.
   CPC .............. *A61M 1/267* (2014.02); *A61M 1/34* (2013.01); *A61M 1/342* (2013.01); *A61M 1/3434* (2014.02); *A61M 1/3441* (2013.01); *A61M 1/3496* (2013.01); *A61M 1/3603* (2014.02); *A61M 1/3621* (2013.01); *A61M 1/3626* (2013.01); *A61M 1/3639* (2013.01); *A61M 1/3653* (2013.01); *A61M 1/3666* (2013.01); *A61M 1/3679* (2013.01); *A61M 2202/203* (2013.01); *A61M 2202/206* (2013.01); *A61M 2205/0238* (2013.01); *A61M 2205/12* (2013.01); *A61M 2205/3334* (2013.01); *A61M 2205/3337* (2013.01); *A61M 2205/7509* (2013.01); *A61M 2205/7518* (2013.01); *A61M 2250/00* (2013.01)
(58) Field of Classification Search
   CPC .. A61M 1/342; A61M 1/3434; A61M 1/3441; A61M 1/3496; A61M 1/3603; A61M 1/3621; A61M 1/3626; A61M 1/3639; A61M 1/3653; A61M 1/3666; A61M 1/3679; A61M 2202/203; A61M 2202/206; A61M 2205/0238; A61M 2205/12; A61M 2205/3334; A61M 2205/3337; A61M 2205/7509; A61M 2205/7518; A61M 2250/00

See application file for complete search history.

(56) References Cited

U.S. PATENT DOCUMENTS

| | | |
|---|---|---|
| 2005/0182349 A1 | 8/2005 | Linde et al. |
| 2005/0236329 A1 | 10/2005 | Brotherton et al. |
| 2008/0234623 A1 | 9/2008 | Strauss et al. |
| 2011/0226686 A1 | 9/2011 | Maurer |
| 2011/0244443 A1* | 10/2011 | van Rijn .......... G01N 33/57492 435/2 |
| 2011/0253629 A1 | 10/2011 | Jovanovic et al. |
| 2012/0226258 A1 | 9/2012 | Otto et al. |
| 2013/0115070 A1 | 5/2013 | Baumgartner et al. |
| 2015/0165105 A1 | 6/2015 | Beden et al. |
| 2015/0273127 A1 | 10/2015 | Flieg et al. |
| 2016/0271311 A1 | 9/2016 | Matheis |
| 2018/0117231 A1 | 5/2018 | Matheis et al. |
| 2018/0140764 A1 | 5/2018 | Georg et al. |

FOREIGN PATENT DOCUMENTS

| | | |
|---|---|---|
| DE | 19622184 A1 | 12/1997 |
| DE | 102009051806 A1 | 5/2011 |
| GN | 103251996 A | 8/2013 |

OTHER PUBLICATIONS

International Search Report and Written Opinion issued in corresponding International Patent Application No. PCT/EP2017/082781 (with English translation of International Search Report) dated Mar. 23, 2018 (14 pages).

International Preliminary Report on Patentability issued in corresponding International Patent Application No. PCT/EP2017/082781 dated Jun. 18, 2019 (8 pages).

\* cited by examiner

SYSTEM FOR EXTRACORPOREAL BLOOD TREATMENT, TREATMENT APPARATUS, KIT AND METHOD FOR OPERATING A SYSTEM FOR EXTRACORPOREAL BLOOD TREATMENT

This application is a National Stage Application of PCT/EP2017/082781, filed Dec. 14, 2017, which claims priority to German Patent Application No. 10 2017 210 134.2, filed Jun. 16, 2017 and German Patent Application No. 10 2016 014 892.6, filed Dec. 15, 2016.

FIELD OF THE INVENTION

The present invention relates to a system for extracorporeal blood treatment, wherein the system comprises a first inlet for introducing a bloodstream to be treated into the system, at least one blood treatment apparatus, as well as a first outlet for discharging a treated bloodstream from the system. The invention further relates to a treatment apparatus having such a system as well as a kit containing the components of the system. The invention furthermore relates to a method for operating such a system and/or treatment apparatus having such a system. The invention further relates to a method for the extracorporeal treatment of blood using such a system or such a treatment apparatus.

BACKGROUND OF THE INVENTION

Systems for extracorporeal blood treatment are generally known in the prior art. Systems are thereby also known which enable two different blood treatments to be combined. Corresponding methods for extracorporeal blood treatment with the aforementioned systems are likewise known.

A system for peritoneal dialysis having an oxygenator arranged in an extracorporeal circulatory system is for example known from WO 2015/067232 A1.

DE 196 22 184 A1 describes a multifunctional device for multifunctional extracorporeal blood treatment with which both a gas exchange treatment as well as a dialysis treatment are possible.

Further known, for example from EP 2 735 326 A1 or EP 0 236 0 509 B1, is combining extracorporeal dialysis treatment for continuous renal replacement therapy (CRRT) with extracorporeal adsorption treatment for treating sepsis in a common extracorporeal blood circulation circuit.

EP 2 735 326 A1 discloses a blood treatment system comprising two dialyzers each containing hollow fiber membranes designed to be series-connected in an extracorporeal blood circulation circuit for treating blood and perfused consecutively, wherein one of the two dialyzers comprises an adsorbent material.

EP 0 236 0 509 B1 likewise teaches arranging a dialyzer and an adsorbent in one series-connected extracorporeal blood circulation circuit for combining dialysis treatment and adsorption treatment.

Further known is combining an extracorporeal dialysis treatment for continuous renal replacement therapy with an extracorporeal gas exchange treatment for removing CO2 from the blood (ECCO2R=Extracorporeal CO2 Removal) in a common extracorporeal blood circulation circuit or for extracorporeal respiration with simultaneous oxygenation (ECMO=Extracorporeal Membrane Oxygenation).

Moreover, a blood treatment apparatus having a gas exchange apparatus is known from EP 2 461 847 B1 which enables an adsorption treatment in addition to the gas exchange treatment, wherein the gas exchange apparatus comprises a carrier for that purpose which is coated with substances for the adsorptive removal of toxins of biological and chemical synthetic origin, their metabolites and degradation products present in blood, blood substitutes or solutions to be introduced into the human and/or animal blood circulation.

In view of the above, the task of the invention is that of providing an improved system for the extracorporeal treating of blood, in particular a system for extracorporeal blood treatment which can expand the extracorporeal treatment possibilities and which offers additional treatment possibilities, in particular respectively flexible manner depending on the respective case of treatment, without needing to lay a further patient access point or establish a further additional extracorporeal blood circuit. A further task of the invention is providing a corresponding treatment apparatus, a corresponding kit, a corresponding method for operating such a system and/or a corresponding treatment apparatus as well as a corresponding method for extracorporeal blood treatment.

SUMMARY OF THE INVENTION

These tasks are solved according to the invention by a system for extracorporeal blood treatment as described herein, by a treatment apparatus as described herein, by a kit as described herein, by a method for operating such a system and/or such a treatment apparatus, as described herein, as well as by a method for extracorporeal blood treatment using such a system or such a treatment apparatus, as described herein. Advantageous implementations of the invention are described in the claims, the description, and the figures, and will be described in greater detail in the following.

A system according to the invention for extracorporeal blood treatment comprises a first inlet for introducing a bloodstream to be treated into the system, at least one first blood treatment apparatus, one second blood treatment apparatus, one third blood treatment apparatus, and a first outlet for discharging a treated bloodstream out of the system.

The first blood treatment apparatus comprises an adsorber apparatus for removing at least one exogenous and/or at least one endogenous pathogen and/or a plasma separator apparatus for separating blood plasma from the other blood components or is an adsorber apparatus and/or a plasma separator apparatus.

The second blood treatment apparatus is designed as a dialysis apparatus, in particular as a dialysis apparatus for renal replacement therapy, preferably for continuous renal replacement therapy.

The third blood treatment apparatus is designed as a gas exchange apparatus, in particular as a gas exchange apparatus for at least partially removing CO2 from a stream of blood flowing through the gas exchange apparatus and/or for supplying a gas or gas mixture into a stream of blood flowing through the gas exchange apparatus.

In a functional state of system application, the first, second and third blood treatment apparatus are thereby sequentially connected in series between the first inlet and the first outlet of the system relative to a direction of blood flow of a bloodstream to be treated and can be consecutively perfused extracorporeally by a bloodstream to be treated. The order to the arrangement of blood treatment apparatus thereby preferably depends on the respective application.

To be understood by extracorporeal blood treatment in the sense of the present invention is a blood treatment occurring external of the human or animal body, wherein extracorporeal blood treatment as such is generally known from the prior art.

To be understood by a bloodstream in the sense of the present invention is a flow of mass containing blood components.

To be understood by a blood treatment apparatus in the sense of the present invention is an apparatus which is able to treat a blood mass, in particular a bloodstream; i.e. change its composition.

To treat blood extracorporeally, a bloodstream to be treated, in particular the blood to be treated; i.e. so-called whole blood, which usually contains all of the blood components existing in the blood, or a bodily fluid to be treated which contains blood components such as e.g. plasma or the like, can be supplied to a system according to the invention via the first inlet as well as discharged out of the system via the first outlet of the system.

In one embodiment of the inventive system, the bloodstream to be treated can be supplied from a reserve storage such as, for example, from a blood bag; i.e. from stored blood or the like, and/or the system can be supplied directly from a patient or animal to be treated.

The treated bloodstream can be emptied into a storage, for example likewise into an appropriate reserve storage bag or the like, and/or supplied to a separated transplantation organ for its supply and/or directly supplied to a patient or animal to be treated.

Particularly preferentially, a system according to the invention for extracorporeal blood treatment is designed to be introduced into the human and/or animal blood circulation and in particular be incorporated into the intracorporeal blood circulation of a patient or animal to be treated by establishing an extracorporeal blood circuit.

In one preferential embodiment of the inventive system, the system is designed to be incorporated veno-venous (VV) or arterio-venous (AV) into the intracorporeal blood circulation of a patient or animal. Depending on application, the veno-venous or the arterio-venous incorporation of an inventive system into the intracorporeal blood circulation of a patient or animal to be treated can be more advantageous. It depends in particular on the blood treatment or blood treatments required or, respectively, the combination of blood treatments required. In a further embodiment, the inventive system can also be incorporated into the intracorporeal blood circulation of a patient or animal by means of one or more artificially created blood access points such as e.g. a fistula or a shunt.

With an inventive system for extracorporeal blood treatment, all variants are in principle possible with respect to the order of the arrangement of the individual blood treatment apparatus in the direction of blood flow, with there hereby being a total of 3!=6 arrangement possibilities, whereby some of these arrangement options have particular advantages which will be described in greater detail further below in this application.

Preferably, the first inlet and/or the first outlet of a system according to the invention is/are formed by tube lines preferably having in each case at least one corresponding connection, or preferably in each case comprising one or more corresponding tube lines respectively, which can in particular be in each case connected to a blood vessel of a patient or animal to be treated and/or a reserve storage via a suitable access point. The tube lines of an inventive system can thereby form a tubing set, in particular a replaceable tubing set.

Preferentially, an inventive system for extracorporeal blood treatment comprises a supply line for introducing, in particular supplying, a bloodstream withdrawn from a patient and/or from an animal and/or from a reserve storage into the system and/or a return line for the emptying, in particular discharging, of a treated bloodstream out of the system and/or for returning the treated bloodstream or a portion thereof into the intracorporeal blood circulation of a patient or animal to be treated and/or into a reserve storage or a separated transplantation organ.

In one preferential embodiment of an inventive system, the system comprises at least one check valve in the return line in order to be able to block the removal and/or discharge of the treated bloodstream from the system, in particular in order to be able to prevent a return into the intracorporeal blood circulation of a patient or animal being treated. Moreover, the return line can comprise a safety apparatus such as, for example, a filter or a magnetic apparatus to stop unwanted particles and in particular prevent and/or inhibit such unwanted particles from passing into the intracorporeal blood circulation.

In sepsis cases, in addition to and frequently concurrent with continuous renal replacement therapy due to kidney failure, artificial respiration is often advisable, in particular for patients in intensive care. An inventive system can perform at least three blood treatments simultaneously and with only one extracorporeal blood circuit, namely a dialysis treatment, an adsorption treatment and/or plasma separation and an extracorporeal gas exchange treatment, in particular extracorporeal artificial respiration in place of or in combination with mechanical ventilation as is needed with intubations or tracheotomies.

Compared to mechanical ventilation, extracorporeal gas exchange treatment has the advantage of being able to relieve the burden on the lungs, whereby they can regenerate better, since the necessary gas exchange ensues by means of the gas exchange apparatus and no longer with the lungs as in mechanical ventilation. Therefore, particularly in cases affecting the lungs, which is frequently exactly what happens in sepsis cases, extracorporeal artificial respiration by means of a gas exchange apparatus is more advantageous than mechanical ventilation. When combined with mechanical ventilation, the latter can be a less intensive procedure, which puts less stress on the patient.

Furthermore, the inventive series connection of adsorber apparatus and/or plasma separator apparatus, dialysis apparatus and gas exchange apparatus requires only one extracorporeal blood circuit. Consequently, patients who are not stable enough to simultaneously supply two extracorporeal blood circuits or whose condition does not permit a delayed extracorporeal blood treatment can also undergo a simultaneous extracorporeal blood treatment comprising an adsorption treatment and/or a plasma separation, in particular a plasma treatment, a dialysis treatment and a gas exchange treatment using an inventive system. Furthermore, fewer access points are needed with only one extracorporeal blood circuit. This thus reduces the stress on the patient as well as the risk of infection.

By means of the sequential arrangement of an adsorber apparatus and/or a plasma separator apparatus, a dialysis apparatus as well as a gas exchange apparatus, a system according to the invention simultaneously enables, for example, a sepsis treatment, a dialysis treatment for renal insufficiency or kidney failure, as well as extracorporeal ventilation.

An adsorber apparatus in the sense of the present invention is an apparatus which is designed to remove one or more components of the bloodstream flowing through the adsorber apparatus from said bloodstream by means of adsorption. Adsorber apparatus are generally known from the prior art.

In one advantageous embodiment of an inventive system, the first blood treatment apparatus is an adsorber apparatus, in particular an adsorber apparatus designed for endotoxin adsorption, for cytokine adsorption and/or for immunoadsorption or comprises such an adsorber apparatus. In particular, the adsorber apparatus is designed to remove at least one foreign pathogen, for example to remove at least one pharmaceutical and/or at least one medical drug and/or at least one phytotoxin and/or at least one organic toxin and/or other toxic substance and/or bacteria, viruses, fungi and/or other organisms, and/or to remove at least one foreign pathogen, for example to remove at least one immune complex and/or at least one immunoglobulin and/or at least one inflammatory response substance of the body (mediator) and/or antibodies and/or to remove at least one so-called "pathogen-associated molecular pattern" (PAMP) and/or at least one so-called alarmin ("danger or damage-associated molecular pattern"—DAMP).

A plasma separator apparatus in the sense of the present invention is an apparatus by means of which blood plasma in a volume of blood introduced into the plasma separator apparatus can be at least partially separated from the remaining blood volume components. A plasma separator apparatus comprises in particular a plasma filter and/or a centrifuge device or is configured as a plasma filter or centrifuge.

The dialysis apparatus of a system according to the invention for extracorporeal blood treatment is preferentially designed to perform at least one procedure from among a group of various hemopurification procedures, preferably for continuous renal replacement therapy; i.e. for CRRT therapy, in particular hemodialysis, hemofiltration, hemodiafiltration, hemoperfusion and/or peritoneal dialysis, whereby the principles behind such dialysis apparatus as well as the associated dialysis procedures are likewise known from the prior art.

The gas exchange apparatus of an inventive system is preferably designed to at least partially remove $CO_2$ and/or enrich a bloodstream with a gas and/or a gas mixture, in particular enriching with oxygen ($O_2$) and/or with a medical gas mixture, wherein particularly gas exchangers designed for $CO_2$ removal and for $O_2$ or gas mixture enrichment of a bloodstream (so-called "oxygenators") are generally known from the prior art. So-called membrane oxygenators are frequently used, the extracorporeal gas exchange treatment associated with their use usually being called extracorporeal membrane oxygenation (ECMO).

In one preferential embodiment of an inventive system, the system, in particular the gas exchange apparatus, comprises an oxygenator from the Novalung GmbH or the Medos Medizintechnik AG company, particularly a Novalung GmbH oxygenator sold under the iLA® name or one from the so-called "hilite" product family of Medos Medizintechnik AG.

In one preferential embodiment of an inventive system, the, system, in particular the gas exchange apparatus, comprises an oxygenator configured as per DE 10 2005 039 446 A1 or consists of such an oxygenator having an integrated blood pump for pumping the bloodstream to be treated through the oxygenator.

In one preferential embodiment of an inventive system for extracorporeal blood treatment, the gas exchange apparatus comprises a membrane oxygenator which is at least partly, preferably entirely, configured as described in DE 10 2008 045 621 A1, EP 3 090 769 A1 or EP 3 090 768 A1, or consists of such an oxygenator.

Particularly preferentially, a system according to the invention, in particular the gas exchange apparatus of an inventive system, comprises a plate-shaped membrane oxygenator with a membrane module having hollow fiber membrane mats stacked on top of each others in layers, wherein preferably at least two overlying mats are arranged at a defined angle offset from one another, in particular offset from one another by an angle of 90°, relative to a medial longitudinal extension of the individual hollow fibers of the hollow fiber membrane mats. Particularly preferential, the individual hollow fiber membrane mats are thereby potted together such that the oxygenator has a rectangular, in particular square, or a round, in particular circular, flow cross section.

Such a plate-shaped membrane oxygenator has the advantage of enabling the setting of a particularly advantageous flow and being able to keep the resulting drop in pressure particularly low, in some cases less than 5 mmHg. This can be particularly advantageous in some cases of treatment, in particular in treatment cases in which combining an extracorporeal adsorption treatment, an extracorporeal dialysis treatment and an extracorporeal dialysis treatment is indicated.

Since, in most applications, the heart of a patient or animal to be treated has insufficient pumping ability to pump the bloodstream to be treated through the system or a veno-venous access to establish the extracorporeal blood circuit for the extracorporeal blood treatment with an inventive system is more advantageous; i.e. the bloodstream to be treated is withdrawn from a vein and the treated bloodstream is likewise returned via a vein, in one advantageous embodiment the inventive system comprises at least one first pump, in particular a first pump designed as a blood pump, for pumping at least a portion of a bloodstream to be treated, wherein the first pump is preferably arranged between the first inlet in the blood flow direction and the first blood treatment apparatus in the blood flow direction and is in particular designed to pump the entire bloodstream to be treated. In other words, in one advantageous embodiment of an inventive system, the first pump is preferably series-connected to three blood treatment apparatus and, particularly preferentially, arranged immediately downstream of the first inlet and upstream of the first blood treatment apparatus relative the direction of the blood flow.

In some cases it can be more advantageous when using the inventive system according to function for the first pump to be arranged between the first blood treatment apparatus and the second blood treatment apparatus or between the second blood treatment apparatus and the third blood treatment apparatus or even only downstream of the third blood treatment apparatus, in each case relative to the direction of the blood flow.

In one particularly preferential embodiment, an inventive system comprises a plurality of pumps, in particular a plurality of pumps respectively designed as blood pumps for pumping the bloodstream to be treated, same being preferably series-connected to the treatment apparatus in the blood flow direction and in particular arranged in the direction of blood flow such that they set the respective pressure ratios necessary for optimal treatment at one or more of the blood treatment apparatus.

In one preferential embodiment, an inventive system comprises a tubing roller pump as the first pump. In a particularly preferential embodiment, the inventive system comprises a centrifugal pump as the first pump. This can be a diagonal pump designed as a rotor pump, wherein the pump preferably comprises a blood-carrying part decoupled from a drive part and the rotor of the pump is in particular supported by a preferably pin-mounted bearing ball, particularly of ceramic or aluminum oxide, and preferably has permanent magnets on its underside facing the drive part and can be driven via magnetic coupling. Particularly preferentially, at least one pump is designed such that only low pump shear stress occurs during perfusion and the individual blood components, in particular the red blood corpuscles, thus suffer as little damage as possible.

In one particularly preferential embodiment, a system according to the invention comprises a pump designed as the blood pump described in DE 10 2010 024 650 A1. Preferably, the dimensions of the blood pump, in particular its connection geometry, is thereby selected so as to adapt to the respective bloodstream to be pumped or, respectively, to the size and/or volume of blood of the patient or animal to be treated.

Since the effectiveness of hemofiltration blood treatment is subject to a pressure gradient on a hemofilter, in particular a hydrostatic pressure gradient between the two sides of the filter membrane, the so-called transmembrane pressure (TMP), it is advantageous with respect to an optimal hemofiltration blood treatment result for an inventive system for extracorporeal blood treatment designed for hemofiltration or hemodiafiltration and/or a dialysis apparatus of an inventive system designed for hemofiltration or hemodiafiltration to comprise at least one blood pump to pump at least a portion of the bloodstream to be treated, by means of which a pressure generated on at least one blood treatment apparatus and/or a resultant pressure gradient, in particular a resulting transmembrane pressure on the dialysis membrane of the dialysis apparatus, can be set to a defined value by modifying the flow of the bloodstream.

Preferentially, to set a defined transmembrane pressure, an inventive system comprises a plurality of correspondingly designed and controllable pumps, in particular different correspondingly designed and correspondingly controllable pumps such as, for example, one or more blood, dialysate, filtrate and/or substituate pumps, with which the bloodstream flow can be set such that a desired defined transmembrane pressure results on the hemofilter of the dialysis apparatus.

In a further advantageous embodiment of an inventive system, the system comprises a further, in particular second, inlet for the addition of a first compound into the bloodstream, in particular into the bloodstream to be treated, wherein this further inlet is preferably arranged in the direction of blood flow such that the first compound can be fed into the bloodstream upstream of the first pump and/or upstream of the first of the three blood treatment apparatus, in particular upstream of the adsorber apparatus, in the direction of blood flow.

Preferentially, this further, in particular second, inlet is thereby designed for the addition of a liquid anticoagulant, in particular for the addition of an anticoagulating citrate solution. An inventive system is thereby particularly preferentially designed such that the first compound, in particular an anticoagulant, can be supplied to the bloodstream no later than prior to a treatment segment of the first treatment device; i.e. upstream of the first treatment device. Particularly advantageous is for the second inlet to thereby be arranged such that the addition can occur upstream of the first pump; i.e. prior to the first pump in the direction of blood flow. Doing so can reduce the risk of clotting within the system, in particular within an adsorber apparatus arranged farther downstream.

Clotting refers to a coagulating; i.e. an agglutinating, of blood components.

A treatment segment in the sense of the invention refers to a flow route along which an actual blood treatment occurs.

It has proven advantageous in some cases for a system according to the invention to comprise a further, in particular second, separate pump for pumping the first compound into the bloodstream to be treated, in particular for pumping the first compound out of a first reserve storage in which the first compound is accommodated. The reserve storage, in which the first compound is preferably accommodated, is preferably a reserve storage bag or an accordingly comparably designed container for storing the first compound, in particular a container which enables sterile storage at sufficient compound shelf life.

Since not only molecules from which the bloodstream to be treated is to be purified can normally pass through the filter membrane, the so-called hemofilter, of the dialysis apparatus in hemofiltration and hemodiafiltration but also a portion of the plasma fluid passes through the hemofilter and is carried away as effluent, it is usually necessary in these cases; i.e. in particular in cases in which the dialysis apparatus is designed for hemofiltration or hemodiafiltration, for a substituate, generally a physiological substitution fluid, in particular an electrolytic solution, to be supplied to the bloodstream to make up for the resultant loss of fluid. The substituate can in principle thereby be introduced before and/or after the dialysis treatment. In some of these applications, it is more advantageous for the substituate not to be supplied to the bloodstream until after the dialysis treatment; i.e. in particular not until after the hemofilter, whereby it is particularly advantageous in some cases for it to not be supplied until immediately prior to the treated blood mass flow being returned into the intracorporeal blood circulation of a patient or animal to be treated.

In hemodialysis; i.e. when the dialysis apparatus is designed for hemodialysis or for hemodiafiltration, the effluent can draw calcium from the bloodstream, in particular when an anticoagulating citrate solution is added to the bloodstream, same which is likewise to be balanced out, whereby a calcium loss resulting therefrom is to be balanced preferentially downstream of the dialysis apparatus, in particular not until after the last blood treatment apparatus.

In a further advantageous embodiment of a system according to the invention, an inventive system therefore comprises a further, in particular a third, inlet for the addition of a second compound into the blood mass flow, in particular for adding a second compound into the treated blood mass flow, wherein this further inlet is preferably arranged in the direction of blood flow such that the second compound can be fed into the blood mass flow downstream of the dialysis apparatus in the direction of blood flow, in particular downstream of the last blood treatment apparatus.

This further, in particular third, inlet is thereby in particular designed for the addition of a second compound in the form of a substituate to offset a fluid loss resulting from hemofiltration or hemodiafiltration and/or for the addition of a second compound in the form of a liquid calcium solution to offset a fluid loss resulting from hemodialysis.

In other words, this means that in one preferential embodiment of an inventive system for extracorporeal blood treatment, a second compound can be added to the blood mass flow preferably after the treatment segment of the dialysis apparatus and/or after a dialysis procedure. Particularly preferentially, the second compound can thereby be fed into the bloodstream in particular immediately prior to being returned into the intracorporeal blood circulation, in particular introduced directly into the return line.

In some cases, it has proven advantageous for an inventive system to comprise a further pump for pumping the second compound, in particular a third pump, which is in particular designed to pump the second compound into the bloodstream from a second reserve storage in which the second compound is accommodated.

In some cases, however, it can also be advantageous for a further, in particular separate, inlet to be provided for supplying the necessary substitute to balance out a loss of fluid or volume in the dialysis apparatus from hemofiltration or hemodiafiltration, in particular an inlet additionally to the third inlet or to the inlet provided for offsetting a calcium loss respectively.

It can be advantageous in some cases for the respective inlet for supplying the substituate to be arranged in the direction of blood flow such that the substituate can be introduced into the bloodstream prior to the gas exchange treatment in the direction of blood flow, whereby the associated inlet is in particular arranged immediately prior to the gas exchange apparatus, relative to the blood flow direction, in order to be able to balance out potential unwanted $CO_2$ loading of the substituate by the gas exchange apparatus. In some applications, it is more advantageous for the substituate to not be added to the bloodstream until after the dialysis and adsorption treatment so as to prevent a dilution effect which would reduce the effectiveness of the adsorption treatment (as a rule, adsorption force is dependent on concentration).

As already noted above, the adsorber apparatus and/or the plasma separator apparatus, the dialysis apparatus and the gas exchange apparatus can in principle be series-connected in any order in an inventive system, wherein, however, certain arrangements; i.e. a certain order to the perfusion of the individual treatment apparatus in the direction of blood flow, are particularly advantageous.

One particularly advantageous embodiment of a system according to the invention for extracorporeal blood treatment is rendered when the adsorber apparatus and/or the plasma separator apparatus is/are arranged upstream of the gas exchange apparatus in the blood flow direction. Since after an adsorption treatment, a substituate, usually a physiological substitution liquid, preferably an electrolytic solution, is likewise supplied to the blood mass flow to make up for the volume withdrawn during the adsorption treatment, which in some cases can be $CO_2$-loaded, it is advantageous for the adsorber apparatus to be arranged upstream of the gas exchange apparatus in the direction of blood flow since an unwanted $CO_2$ loading effected by the gas exchange apparatus can in this way be rebalanced. This can thereby result in achieving improved $CO_2$ removal from the blood mass flow to be treated compared to an arrangement of the gas exchange apparatus upstream of the adsorber apparatus.

In an alternative, in some cases likewise advantageous, embodiment of an inventive system, the adsorber apparatus and/or the plasma separator apparatus is/are arranged downstream of the gas exchange apparatus in the blood flow direction. Advantageous with this arrangement is that the hydrostatic pressure on the adsorber apparatus can result in an increased pressure gradient in the gas exchange apparatus, in particular on the gas exchange membrane, whereby the gas exchange can be improved.

To supply the necessary substituate to offset the loss in volume in the adsorber apparatus during the adsorption treatment, an inventive system preferably comprises a further, in particular a fourth, inlet to the blood mass flow which is in particular arranged in the direction of blood flow such that the substituate can be supplied after the absorption process in the direction of blood flow, in particular downstream of the treatment segment in the adsorber apparatus, whereby the fourth inlet is in particular arranged immediately downstream of the adsorber apparatus relative to the blood flow direction.

In some cases, however, it can be (more) advantageous for the fourth inlet to be arranged upstream of the adsorber apparatus, in particular upstream of the gas exchange apparatus, in order to balance out an undesired $CO_2$ loading of the bloodstream by the gas exchange device via the substitution liquid necessary for offsetting the fluid loss resulting from the adsorption treatment. This is in particular the case when the adsorber apparatus is arranged after the gas exchange apparatus in the direction of blood flow; i.e. downstream of the gas exchange change.

In a further advantageous embodiment of an inventive system, the adsorber apparatus and/or the plasma separator apparatus is/are arranged upstream of the dialysis apparatus in the direction of blood flow, particularly when the dialysis apparatus is designed for hemodialysis or hemodiafiltration and in particular comprises a dialyzer. The upstream arrangement of the adsorber apparatus in the bloodstream; i.e. ahead of the dialysis apparatus in the blood flow direction, has the advantage of the adsorber apparatus not being supplied with any flow of dialysate-diluted blood, whereby particularly high adsorption treatment efficiency can be achieved.

Furthermore, the dialysis apparatus being arranged downstream can counterbalance nonspecific electrovalences or pH shifts developing in the adsorber.

Moreover, due to it being composed of minute hollow fibers, the dialysis apparatus arranged downstream in the bloodstream can act as a safety system against unwanted introduction of particles from the adsorber apparatus.

If the dialysis apparatus of a system according to the invention is designed for hemodialysis or hemodiafiltration and comprises in particular a dialyzer, an inventive system, in particular the dialysis apparatus, preferably comprises a fifth inlet for supplying a dialysate; i.e. a dialysis fluid.

To remove effluent forming in the dialysis apparatus during the dialysis treatment, the inventive system preferably comprises a second outlet.

In an alternative embodiment of a system according to the invention, the adsorber apparatus is arranged downstream of the dialysis apparatus in the direction of blood flow, particularly if the dialysis apparatus is designed for hemofiltration or hemodia-filtration and preferably comprises a hemofilter. This sequence can be advantageous in some applications, in particular when a particularly effective adsorption treatment is indicated since, in this case, the bloodstream to be treated can be concentrated in the dialysis apparatus by the hemofiltration, whereby the effectiveness of the adsorption treatment can be increased in the subsequently arranged adsorber apparatus.

In this case, although the system's clotting risk increases compared to the previously described embodiments of an inventive system, in particular in the adsorber apparatus, any clotting which does begin can in many cases be relatively reliably and promptly identified by applicable monitoring measures such as, for example, respective pressure sensors arranged before and after at least one blood treatment apparatus, by means of which the condition of the respective blood treatment apparatus can be deduced. The clotting risk can thereby be well-controlled in most cases, particularly in conjunction with the additional use of anticoagulants.

In a further advantageous embodiment of an inventive system, the dialysis apparatus is arranged upstream of the gas exchange apparatus in the direction of blood flow, particularly when the dialysis apparatus is designed for hemodialysis or hemofiltration and requires the supply of a dialysate for dialysis treatment. In this case, unwanted CO2 loading can under some circumstances be balanced by CO2-loaded dialysate in the dialysis apparatus by means of the gas exchange apparatus sequentially arranged downstream of the dialysis apparatus in the blood flow direction prior to the treated bloodstream being returned into the intracorporeal blood circulation of a patient or animal to be treated, which would not be the case with an arrangement of the dialysis apparatus downstream of the gas exchange apparatus.

In an alternative, but in some cases equally advantageous embodiment of an inventive system, the dialysis apparatus is arranged downstream of the gas exchange apparatus in the direction of blood flow, whereby, in this case, the dialysis apparatus is preferably designed for hemofiltration, comprises a hemofilter and is in particular not designed for hemodialysis.

The hemofilter downstream of the gas exchange apparatus can increase the pressure gradient between the gas exchange apparatus blood side and gas side, whereby the efficiency of the gas exchange apparatus can be improved.

When the dialysis apparatus is designed only for hemofiltration and not for hemodialysis, particularly also not for hemodiafiltration, the disadvantage of unwanted CO2 loading due to a bloodstream exchange with a supplied, potentially CO2-loaded dialysate does not arise as is possible in hemodialysis or hemodiafiltration. In the latter case, the substitution volume replacement solution can preferably be supplied upstream of the gas exchanger so as to at least partially, preferably entirely, offset the potential CO2 loading by the gas exchange apparatus.

Preferentially, a system according to the invention, in particular the gas exchange apparatus, comprises a third outlet for the removal of carbon dioxide (CO2) eliminated from the treated bloodstream and/or a further, in particular sixth, inlet for supplying a gas or gas mixture to enrich the bloodstream to be treated, in particular for supplying oxygen (O2) and/or a medical gas mixture and/or for supplying a flushing gas such as e.g. oxygen (O2), a gas mixture and/or ambient air.

In a further advantageous embodiment of an inventive system, the system comprises at least one pressure sensor device for determining bloodstream flow pressure at least at one defined point in the system, wherein at least one pressure sensor device is preferably arranged directly ahead of and/or directly after at least one treatment segment of a blood treatment apparatus in the blood flow direction.

If pressure sensor devices are in each case provided before and after at least one treatment segment, falling pressure can in this way be detected over the treatment segment, from which the condition of the associated blood treatment apparatus can be deduced. In particular, this allows assessing to what extent a blood treatment apparatus is affected by clotting, whereby an abrupt marked rise in pressure loss indicates that the respective blood treatment apparatus is affected by clotting.

In one preferential embodiment, an inventive system comprises a control device, wherein the control device in the inventive system is in particular designed to control and/or regulate all the controllable and/or adjustable components of the system. In other words, this means that in a preferential embodiment, an inventive system has a common control system for controlling all the blood treatment apparatus. The control system is thereby in particular designed to control one or more pumps and/or to control inflow and/or outflow rates of substances and/or compounds and/or to evaluate sensor data detected by at least one sensor device and/or to monitor the inventive system, in particular for controlling and/or regulating the bloodstream to be treated.

Preferentially, one or more pressure sensor devices can detect blood circulation blockages or disruptions and appropriate measures taken such as, for example, the triggering of an alarm or the switching off of the system, in particular a bloodstream-pumping pump.

Preferably, a system according to the invention is designed such that a defined transmembrane pressure for at least one of the blood treatment apparatus, in particular for the dialysis apparatus, necessary for the highest possible effectiveness of a blood treatment is monitored with regard to a limit value. Preferably, the bloodstream flow can be set as a function of at least one sensor signal detected by a pressure sensor device such that a desired defined transmembrane pressure is set or respectively results so as to enable achieving improved blood treatment.

In a further advantageous embodiment of an inventive system, an inventive system preferably comprises at least one gas bubble detection device for detecting a gas bubble in the bloodstream. Preferably, the system is designed such that should the gas bubble detection device detect a gas bubble, a check valve preferably arranged ahead of the first inlet, preferably in a return line, can be closed in order to prevent the gas bubble from being returned with the treated bloodstream into the intracorporeal circuit, in particular the intracorporeal blood circulation, of a patient or animal to be treated. Furthermore, preferably all the pumps serving in pumping the bloodstream can in addition be switched off.

In a further advantageous embodiment of an inventive system, a treatment segment for at least one blood treatment apparatus is at least partially, preferably entirely, formed by an exchangeable treatment module, in particular by a cartridge-like treatment module. Such a design to a blood treatment apparatus enables flexibly replacing the respective treatment module, in particular simply and flexibly adjusting the individual treatment apparatus to the respectively required blood treatment.

For example, an endotoxin adsorber treatment module can thereby be easily replaced by a cytokine adsorber treatment module having a different functional adsorption layer or a special immune adsorber treatment module or a hemofilter replaced by a dialyzer or the like. Thus, there is a significant increase in the scope of treatments possible with an inventive system, thereby greatly increasing an inventive system's economic efficiency.

In one further advantageous embodiment of an inventive system, the system comprises at least one switchable bypass device for bypassing at least one blood treatment apparatus. An inventive system can thereby also be used if needed for blood treatments which respectively only require the use of one or two of the system's three blood treatment apparatus but do not necessitate the perfusion of all three blood treatment apparatus of an inventive system. In this way, a needed blood treatment which only requires, for example, an adsorption treatment and/or only plasma separation and a dialysis treatment can occur while the gas exchange apparatus is bypassed. Likewise possible is a dialysis treatment with subsequent gas exchange, particularly subsequent CO2 removal, without a simultaneous adsorption treatment. The scope of an inventive system's treatment possibilities can thereby be significantly increased. Furthermore, treatment costs can be significantly reduced in a plurality of treatment cases since material consumption can be greatly lowered due to not all three treatment modules being used in each case. Moreover, a treatment apparatus can be removed from the system when it no longer fulfills its function due, for example, to becoming clotted or expended such as e.g. a fully loaded adsorber.

Preferably, at least one bypass device comprises at least one bypass valve as well as an associated bypass line which is in particular fluidly connected or connectable to a main line, whereby the associated bypass line can in particular be opened or closed by means of a bypass valve so that a bloodstream to be treated can be precisely routed along the associated bypass line or precisely channeled through the subsequent blood treatment apparatus or the subsequent blood treatment apparatus segment respectively.

Preferentially, at least one bypass valve is thereby designed such that there is no perfusion of the downstream treatment segment when the bypass valve is open; i.e. the subsequent blood treatment apparatus can preferably be completely closed off and the entire bloodstream to be treated can bypass the respective blood treatment apparatus via the associated bypass line; i.e. the blood treatment apparatus can be circumvented.

To be particularly understood by "blood treatment apparatus bypass" in the sense of the present invention is a branching of the main line, particularly at a branching point upstream of the blood treatment apparatus or in the blood treatment apparatus, a bypass line bypassing the blood treatment apparatus, and the bypass line rejoining the main line again downstream of, in particular subsequent, the blood treatment apparatus or in the blood treatment apparatus.

On the other hand, when the bypass valve is closed, the bypass line is preferably closed, particularly completely, so that the entire bloodstream being treated perfuses through the downstream treatment segment or downstream blood treatment apparatus respectively.

Doing so enables the selective perfusion of only the required treatment apparatus. The possible applications of a system according to the invention can thus be increased significantly. In particular, the utilization or useful life respectively of an inventive system can thereby be improved, which can in turn increase the economic efficiency.

To set a defined bloodstream flow rate at least at one of the blood treatment apparatus, in particular to produce a desired defined transmembrane pressure, particularly for at least one associated treatment segment, a system according to the invention can comprise at least one further pump in particular arranged in a section between a branching point and the subsequent merging with the main line and/or the bypass line.

The appropriate number and design of the individual pumps can in this way achieve independent blood flow rate settings in the individual treatment apparatus, wherein the system in particular comprises one or more correspondingly designed control devices to that end.

In one advantageous embodiment, at least one bypass line associated with a blood treatment apparatus is designed such that a recirculating blood flow can be effected by and/or through the associated blood treatment apparatus.

In a further advantageous embodiment of an inventive system, at least one further blood treatment apparatus is arranged in the associated bypass line, in particular in such a manner that a recirculating blood flow through the associated blood treatment apparatus arranged in the main line and/or through the further blood treatment apparatus arranged in the bypass line results.

In an alternative advantageous embodiment of a system according to the invention, the first blood treatment apparatus is a plasma separator device preferably able to be bypassed by a bypass line, wherein a further blood treatment apparatus in the form of an adsorber apparatus is arranged in particular in the bypass line. The adsorber apparatus is thereby preferentially arranged downstream of a pump arranged in the bypass line.

The treated blood or blood plasma respectively discharged out of the adsorber apparatus can thereby be fed to the main line downstream of the plasma separator device or recirculated back to the plasma separator device.

In an alternative embodiment of an inventive system, separated plasma from the plasma separator apparatus, in particular by means of a pump, can be discharged and fed to a plasma disposal container and fresh plasma, particularly from a reserve storage device, supplied by means of a further inlet, in particular the main line, preferably with the aid of a further pump.

In a further advantageous embodiment of an inventive system, at least one component of the system has a biocompatible and preferably functional coating on a surface coming into contact with the bloodstream to be treated, in particular an antibacterial, coagulation-inhibiting and/or anti-inflammatory coating. Preferably, at least one lumen of the system configured for perfusion by a bloodstream to be treated and/or treated bloodstream is provided with a biocompatible and preferably functional coating, in particular with an antibacterial, coagulation-inhibiting and/or anti-inflammatory coating.

Preferably at least one surface of the inventive system thereby has a coating containing heparin and/or a coating containing albumin and heparin. It can, however, be advantageous in some cases for the system to only comprise heparin-free coatings so that the system can thereby also be used to treat patients or animals with a heparin intolerance.

In an alternative and/or additionally preferential embodiment of an inventive system, at least one coating has defined antibodies and/or one or more enzymes. An antibacterial coating is also conceivable.

In a further advantageous embodiment of an inventive system, at least one protective layer is applied to protect the functional coating, whereby the protective layer preferably serves in enabling sterilization and/or deposition of individual coated components of the system without the functionality of the functional coating suffering significant loss.

In one particularly preferential embodiment of an inventive system, the system comprises at least one surface having a coating formed using the SPS® technology of the Leukocare AG company.

An inventive treatment apparatus for extracorporeal blood treatment comprises a system for extracorporeal blood treatment designed in accordance with the present invention, wherein the first, the second and the third blood treatment apparatus of the system is in particular arranged in a common housing and/or accommodated by a common base; i.e. by a common carrier device.

Preferably, the three blood treatment apparatus are thereby arranged in a common housing and/or accommodated by a common base such as, for example, a common carrier device or the like. Particularly preferentially, the individual blood treatment apparatus are thereby each replaceably affixed in and/or on the common housing and/or base, in particular as respectively replaceable modules. A particularly compact inventive system can thus be provided which can at the same time be flexibly adapted and designed for the respective case of treatment.

A kit and/or set for extracorporeal blood treatment according to the invention comprises as components at least one first blood treatment apparatus, one second blood treatment apparatus, one third blood treatment apparatus and a tubing set having a first inlet for introducing a bloodstream to be treated and a first outlet for discharging a treated bloodstream via one or more tubes as well as, in particular, an installation and/or operating guide.

The first blood treatment apparatus is thereby an adsorber apparatus for removing at least one exogenous and/or at least one endogenous pathogen and/or a plasma separator apparatus for separating blood plasma from the remaining blood components or comprises a corresponding adsorber apparatus and/or plasma separator apparatus. The second blood treatment apparatus is designed as a dialysis apparatus, in particular as a dialysis apparatus for renal replacement therapy and the third blood treatment apparatus is designed as a gas exchange apparatus, in particular as a gas exchange apparatus for at least partially removing $CO_2$ from a bloodstream flowing through the gas exchange apparatus and/or for supplying a gas or gas mixture into a bloodstream flowing through the gas exchange apparatus. The components of the kit can inventively be combined into an extracorporeal blood treatment system designed according to the present invention, in particular in accordance with the installation and/or operating guide.

So doing enables readily providing a particularly flexible inventive system affording a combination of adsorber apparatus and/or plasma separating device, dialysis apparatus and gas exchange apparatus specifically tailored to the respective case of treatment.

In other words, an inventive system can be provided both in the form of a common treatment apparatus in which the three blood treatment apparatus of the system; i.e. the adsorber apparatus and/or the plasma separator, the dialysis apparatus and the gas exchange apparatus are part of a common apparatus, as well as in the form of a kit and/or a set in which at least two of the three blood treatment apparatus are separate apparatus which are, however, able to be connected to an inventive system by means of an appropriate tubing system having one or more tube lines and sequentially connected in series according to the invention such that the individual blood treatment apparatus can each be sequentially perfused one after the other.

One inventive method for operating an inventive system for extracorporeal blood treatment and/or an inventive treatment apparatus is characterized by the steps:
 providing a volume of blood to be treated,
 introducing a bloodstream to be treated into the system via the first inlet of the system,
 perfusing at least one of the blood treatment apparatus, and
 discharging the treated bloodstream via the first outlet of the system.

Preferably, provided the system used for the extracorporeal blood treatment is designed thereto and comprises at least one particularly switchable bypass device, only those blood treatment apparatus for which use is indicated for the respectively required treatment are thereby perfused depending on said need.

In one advantageous embodiment of a method according to the invention for operating an inventive system, the blood mass to be treated is thereby provided in a receptacle, in particular a container or a bag, wherein the treated blood is preferably discharged into a receptacle, in particular into a container or bag. Alternatively, the treated blood can also be supplied to a separated organ provided for transplant or a patient or animal to be treated.

One method according to the invention for extracorporeal blood treatment with an inventive system or an inventive treatment apparatus is characterized by the steps:
 incorporating the system into the blood circulation of a human or animal to be treated and establishing an extracorporeal blood circuit by connecting the first inlet of the system to a first blood vessel of the human or animal to be treated and connecting the first outlet of the system to the first blood vessel and/or a second blood vessel of the human or animal,
 withdrawing a bloodstream to be treated from the intracorporeal blood circulation of the human or animal and introducing the bloodstream to be treated into the system via the first inlet of the system,
 perfusing at least one of the blood treatment apparatus,
 discharging the treated bloodstream via the first outlet of the system and returning the treated bloodstream into the intracorporeal blood circulation of the human or animal.

Depending on need, the inventive system can thereby be connected to the intracorporeal blood circulation of a human or animal to be treated veno-venous or arterio-venous or, alternatively, via at least one artificially created blood access point.

Particularly well-suited to the veno-venous connecting of an inventive system to an intracorporeal blood circulation of a human or animal to be treated is a double lumen cannula having an inlet and outlet arranged concentrically to one another, for example the cannulas for adult patients marketed under the name of "NovaPort® twin" from the Novalung GmbH company. In other words, in an inventive extracorporeal blood treatment method, a double lumen cannula is preferably used to introduce the system into a blood circulation of a human or animal to be treated and establish the extracorporeal blood circuit.

This and other features of the invention follow from the claims and the description as well as the associated figures and description of the figures, whereby all of the cited and/or depicted features and feature combinations can be realized not only in a configuration of the invention in the respectively indicated combination but also in other combinations or on their own provided same is technically feasible.

Some of the cited and/or depicted features or characteristics of the invention relate both to an inventive system, an inventive treatment apparatus, an inventive kit, an inventive method for operating the inventive system and/or an inventive treatment apparatus as well as to an inventive method for extracorporeal blood treatment with an inventive system or with an inventive treatment apparatus, wherein some of these features and characteristics are only described once, for example only in conjunction with the inventive system, although nonetheless apply equally in the context of technically feasible embodiments to an inventive system as well as to an inventive treatment apparatus, inventive kit, inventive method for operating such a system and/or an inventive treatment apparatus as well as also an inventive method for extracorporeal blood treatment with such a system or with such an inventive treatment apparatus.

BRIEF DESCRIPTION OF THE DRAWINGS

The following will reference the accompanying figures in describing the invention in greater detail based on a plurality of example embodiments, wherein unless expressly identified or contextually indicated otherwise, the same reference numerals are used to identify functionally equivalent components. Shown are.

DETAILED DESCRIPTION

Figure 1:
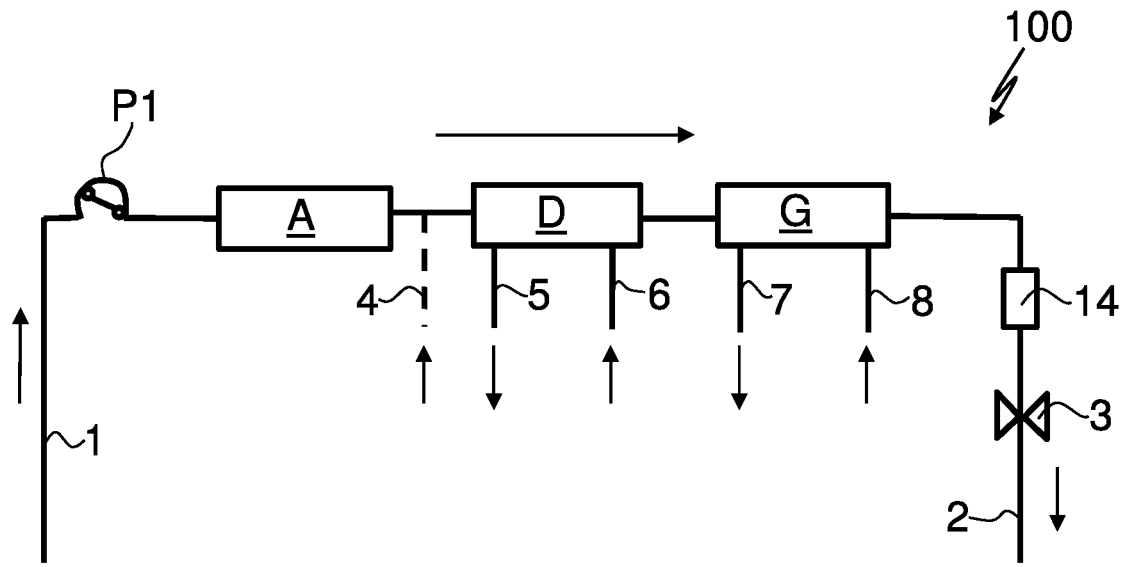
FIG. 1 a schematic representation of the general structure of a first example embodiment of a system according to the invention, FIG. 2 a schematic representation of the general structure of a second example embodiment of a system according to the invention, FIG. 3 a schematic representation of the general structure of a third example embodiment of a system according to the invention, FIG. 4 a schematic representation of the general structure of a fourth example embodiment of a system according to the invention, FIG. 5 a schematic representation of the general structure of a fifth example embodiment of a system according to the invention, FIG. 6 a schematic representation of the general structure of a sixth example embodiment of a system according to the invention, FIG. 7 a schematic representation of the general structure of a seventh example embodiment of a system according to the invention, FIG. 8 a schematic representation of the general structure of an eighth example embodiment of a system according to the invention, FIG. 9 a schematic representation of the general structure of a ninth example embodiment of a system according to the invention, and FIG. 10 a schematic representation of the general structure of a tenth example embodiment of a system according to the invention.

FIG. 1 shows a schematic representation of the general structure of a first example embodiment of an inventive system 100 for extracorporeal blood treatment, wherein the system 100 comprises a first inlet formed by a supply line 1 for introducing a bloodstream to be treated into the system 100, three blood treatment apparatus A, D and G, and a first outlet formed by a return line 2 for discharging a treated bloodstream out of the system 100.

A first blood treatment apparatus A is thereby an adsorber apparatus designed to adsorb endotoxins. A second blood treatment apparatus D is designed as a dialysis apparatus D, in particular for hemodialysis. A third blood treatment apparatus G is an oxygenator for removing carbon dioxide ($CO_2$) from the bloodstream to be treated as well enriching the bloodstream to be treated with oxygen ($O_2$).

The inventive system 100 depicted in FIG. 1 is thereby designed to be introduced into a human or animal blood circulation in order to establish an extracorporeal blood circuit, whereby the supply line 1 can to that end be connected to a first blood vessel of the patient or animal to be treated, in particular a vein or an artery, so as to remove a bloodstream to be treated and the return line 2 to the first blood vessel or a second blood vessel, in particular a vein, so as to return a treated bloodstream into the intracorporeal blood circulation of the patient or animal respectively.

To establish the extracorporeal blood circuit, in particular to connect into the intracorporeal blood circulation of the patient or the animal to be treated, the system can preferably be connected using a double lumen cannula which enables the establishing of a veno-venous extracorporeal blood circuit via just one vascular access point. The stress on the patient or animal to be treated is thereby extremely low since two separate access points to two separate vessels do not need to be placed. Furthermore, the risk of infection is reduced.

According to the invention, the three blood treatment apparatus A, D and G are thereby connected in series; i.e. sequentially, relative to a direction of blood flow of a bloodstream flowing through the system 100, which is symbolized by the arrows in FIG. 1. The individual blood treatment apparatus A, D and G are thereby part of a common inventive treatment apparatus and accommodated on a common base, in particular mounted on a common carrier, wherein the individual components of the system 100 are connected to one another by respective hose lines such that they can be perfused sequentially; i.e. consecutively.

The inventive series connection of an adsorber apparatus A, a dialysis apparatus D as well as a gas exchange apparatus G enables a combined blood treatment, in particular the combination of an adsorption treatment; in the present case, the combination of a sepsis treatment with a dialysis treatment as well as the removal of $CO_2$ from the blood and/or an oxygenation of the blood ($O_2$ enrichment) in one single common extracorporeal blood circuit. Doing so can avoid needing to establish multiple extracorporeal circuits for treating the blood and having to lay the respective multiple access points in a patient or animal to be treated. A system 100 according to the invention thus enables simultaneous adsorption, dialysis and gas exchange blood treatment of the blood volume of only one extracorporeal blood circuit.

The adsorber apparatus A is designed in the present example embodiment of an inventive system 100 for sepsis treatment. Adsorber apparatus as such for this purpose are known in general from the prior art. Since the adsorber apparatus A extracts portions of the blood mass flow volume during the blood treatment, a further, in particular fourth inlet 4 is situated downstream of the adsorber apparatus A in the blood flow direction for supplying a substituate to order to compensate for this volume loss, wherein particularly a fluid substituate, in particular an electrolytic solution, can be supplied.

In the inventive system 100 depicted in FIG. 1, the dialysis apparatus D comprises a dialyzer for hemodialysis which can be fed a dialysate or a dialysis fluid respectively via a fifth inlet 6 and an effluent resulting from the dialysis treatment discharged via a second outlet 5. Dialysis apparatus of this type are likewise generally known in the prior art.

The gas exchange apparatus G is designed as an oxygenator G in the inventive system 100 depicted in FIG. 1, wherein carbon dioxide ($CO_2$) can be removed from the perfusing bloodstream by means of the oxygenator G using a defined gas supplied to the oxygenator via a further, in particular sixth inlet 8, same being able to be discharged via a third outlet 7. The bloodstream flowing through the oxygenator G can thereby be additionally supplied with the defined gas supplied to the oxygenator via the sixth inlet 8 and enriched, in this case, with oxygen ($O_2$). Oxygenators of this type are likewise generally known in the prior art. The oxygenator G can, for example, be an iLA® Membrane Ventilator IL-1000-01 from the Novalung GmbH company.

To pump the bloodstream to be treated through the system 100, a first pump P1 designed as a blood pump is provided, wherein the first blood pump P1 is controlled by a control device (not shown in the present depiction) for the controlling and/or regulating of the bloodstream which is likewise a part of the inventive system 100.

The first blood pump P1 can thereby be a tubing roller pump. In one particularly preferential embodiment, the inventive system has a centrifugal pump as the first pump. This can be a diagonal pump designed as a rotor pump, preferably as that described in DE 10 2010 024 650 A1. The dimensions of the blood pump P1, in particular its connection cross section, is selected according to the volume of blood of the patient or animal to be treated.

In order to be able to set an optimal bloodstream at least at one of the three blood treatment apparatus A, D and/or G for optimal treatment success as well as for monitoring purposes, the system comprises a plurality of pressure sensor devices (not shown in the present depiction), wherein in the present example embodiment of an inventive system 100, a respective pressure sensor device is in each case arranged immediately prior to and immediately following a blood treatment apparatus A, D or G.

This enables respectively determining a resulting pressure gradient of the associated blood treatment apparatus A, D or G, by means of which the condition of the respective blood treatment apparatus A, D or G can be deduced. In particular, the determined pressure gradient enables drawing a conclusion as to the extent to which the respective blood treatment apparatus A, D or G is affected by clotting.

Furthermore, a transmembrane pressure in the respective blood treatment apparatus A, D and/or G can be determined in this way. Since the efficiency of the respective blood treatment is basically a function of the respective transmembrane pressure applied and same should be within a specific range for optimal treatment success based on the respective blood treatment apparatus, the bloodstream can in this way be regulated, in particular by appropriately controlling the blood pump P1, at least with respect to at least one of the three blood treatment apparatus, such that the respectively advantageous transmembrane pressure can be set.

The system 100 according to the invention depicted in FIG. 1 further comprises a gas bubble detection device 14 for detecting a gas bubble in the bloodstream arranged downstream of the three blood treatment apparatus A, D and G in the direction of blood flow as well as a check valve 3 arranged in the return line 2 downstream of the gas bubble detection device 14. If the gas bubble detection device 14 detects a gas bubble in the bloodstream, the check valve 3 is closed, the first blood pump P1 switched off, and an alarm triggered. Doing so can thereby prevent the gas bubble from being returned into the intracorporeal blood circulation of the patient or animal with the bloodstream and thereby leading to a life-threatening condition or even death.

The inventive system 100 described here is thereby designed for a bloodstream in the range of 0.05 to 5l per minute, in particular a bloodstream within a range of from 0.1 to 3l, in particular a range of from 0.2 to 1l per minute, particularly a range of 0.2 to 0.5l per minute.

To prevent complications, the surfaces of the system 100 lumen which come into contact with the bloodstream can be provided with a biocompatible coating and at least partially with at least one functional coating, in particular with an antibacterial, coagulation-inhibiting and/or anti-inflammatory coating.

In the first example embodiment of an inventive system 100 for extracorporeal blood treatment depicted in FIG. 1, the adsorber apparatus A is arranged upstream of the dialysis apparatus D in the direction of blood flow, wherein the dialysis apparatus D is in turn arranged upstream of the gas exchange apparatus G in the direction of blood flow. This arrangement has the advantage of the adsorber apparatus A being able to be supplied an undiluted bloodstream, thereby enabling high adsorption treatment efficiency to be ensured. Furthermore, unwanted nonspecific electrovalences or pH shifts can occur in the adsorber apparatus A, which the dialysis apparatus D can balance out in a dialysis treatment provided downstream in the flow of the bloodstream with the order of the individual blood treatment apparatus A, D and G as depicted in FIG. 1.

Furthermore, the dialysis apparatus D arranged downstream of the adsorber apparatus A in the flow of the bloodstream can act as a further safety system against unwanted introduction of particles from the adsorber apparatus A arranged upstream in the bloodstream flow.

The arrangement of the gas exchange apparatus G downstream of the adsorber apparatus A in the direction of blood flow has the advantage that an enriching of the bloodstream with carbon dioxide ($CO_2$) by the feed of the substitute downstream of the adsorber apparatus A (which can ensue in the example embodiment depicted in FIG. 1 via the fourth inlet 4 downstream of the adsorber apparatus and ahead of the dialysis apparatus) as well as a dialysis fluid potentially loaded with carbon dioxide ($CO_2$) (which can be supplied to the system 100 in this example embodiment via the fifth inlet 6) can be balanced by means of the gas exchange apparatus G prior to the treated bloodstream being returned into the intracorporeal blood circulation of the patient or animal.

If the dialysis apparatus D is designed for hemodiafiltration instead of hemodialysis in a system according to the invention for extracorporeal blood treatment in which the blood treatment apparatus are arranged as described on the basis of FIG. 1, a substitute, in particular an additional quantity of substitute, can be preferentially supplied to the bloodstream via inlet 4 to make up for the fluid loss in the dialysis apparatus D. Alternatively or additionally, the system can also comprise a further inlet in the blood flow direction after the dialysis apparatus D for adding the substitute to compensate for the fluid and/or volume loss in the adsorber apparatus A and/or dialysis apparatus D.

In order to enable the flexible adjustment of the inventive system 100 to the respective blood treatment required, the individual blood treatment apparatus A, D and G of the inventive system 100 comprise respectively replaceable treatment modules which in each case encompass the entire treatment segment and can be easily switched out as a replacement part. The inventive system 100 can in this way be easily and quickly adapted to the respectively required treatment. Thus, for example, the adsorber apparatus A can be quickly and easily reconfigured from an adsorber apparatus A for endotoxin adsorption into an adsorber apparatus A for cytokine adsorption for which specifically designed adsorbent treatment modules are required depending on application.

Correspondingly, the dialysis apparatus D of the inventive system 100 can be reconfigured from a dialysis apparatus D designed for hemodialysis into a dialysis apparatus D designed for hemofiltration or hemodiafiltration by changing the respective dialysis treatment module.

The gas exchange apparatus G of the inventive system 100 can also be adapted in the same way, wherein depending on the treatment required, a gas exchange treatment module can be used which is designed solely for removing $CO_2$ from the bloodstream or a gas exchange treatment module which additionally allows the possibility of enriching the bloodstream to be treated with oxygen ($O_2$) or another gas or gas mixture.

Preferably, the individual inlets and outlets can likewise be adapted and/or reconfigured, in particular with respect to their arrangement within the system, particularly with respect to their arrangement ahead of and/or after the respective blood treatment apparatus.

The system 100 can thereby be specifically configured for each treatment. Furthermore, the individual treatment modules can be quickly and easily replaced should clotting or the like occur. Moreover, this thereby constitutes a particularly simple way to guarantee a sterile system 100 is provided for blood treatment since all of the components which come into contact with the bloodstream, in particular the respective blood treatment modules and their tube connections, can be easily replaced before treatment begins on a new patient or a new animal.

Figure 2:
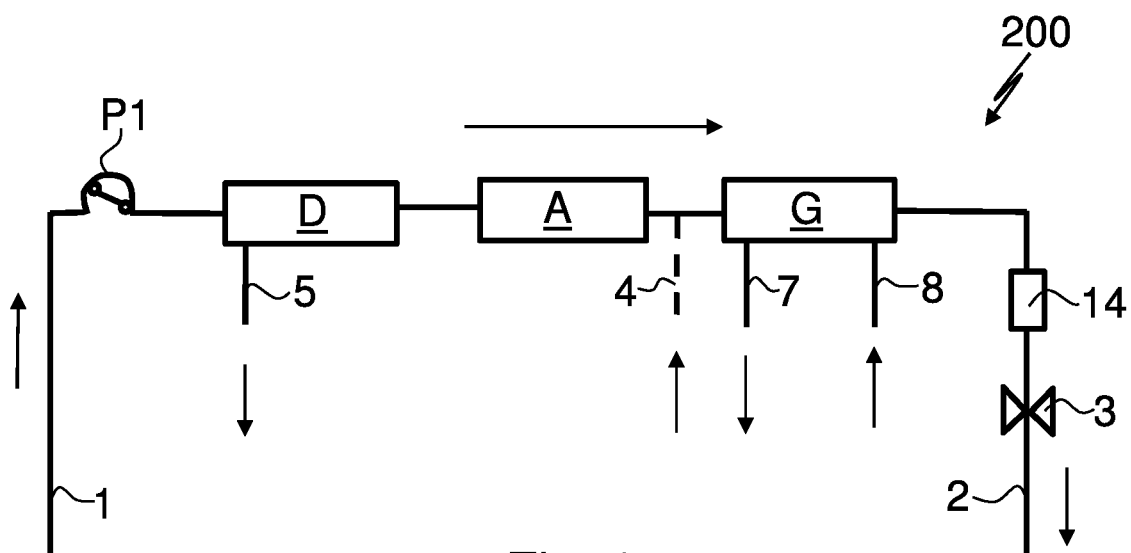

FIG. 2 shows a second example embodiment of an inventive system 200 for extracorporeal blood treatment, wherein components having equivalent functionality exhibit the same reference numerals.

The second example embodiment of a second inventive system 200 for extracorporeal blood treatment likewise depicted only schematically in FIG. 2 is of basically similar structure to the first example embodiment of an inventive system 100 for extracorporeal blood treatment described on the basis of FIG. 1, although differs from the inventive system 100 described on the basis of FIG. 1 with respect to the order of the three blood treatment apparatus A, D and G in the inventive system 200 depicted in FIG. 2 being different and also in that the dialysis apparatus D is not designed for hemodialysis and correspondingly has no dialyzer but is rather designed only for hemdfiltration and correspondingly comprises a hemofilter.

For this reason, the system 200 does not have a fifth inlet 6 for supplying a dialysate since hemofiltration does not require an additional dialysis fluid to be supplied and only one effluent resulting from the hemofiltration needs to be discharged which, in the system depicted in FIG. 2, can likewise occur via the second outlet 5.

The design of an inventive system 200 for extracorporeal blood treatment depicted in FIG. 2, in which the dialysis apparatus D is arranged upstream of the adsorber apparatus A in the direction of blood flow, and thus the bloodstream to be treated perfuses the dialysis apparatus D prior to the adsorber apparatus A, has the advantage of the bloodstream being concentrated by the extraction of the filtration volume (effluent) in the hemofilter of the dialysis device D and the adsorber apparatus A thus being able to be supplied a more strongly concentrated bloodstream than the inventive system 100 of FIG. 1. A higher effectiveness to the adsorption treatment can thus be achieved. Consequently, the inventive system 200 depicted in FIG. 2 can achieve an improved adsorption treatment.

The downstream arrangement of the gas exchange apparatus G in the direction of blood flow in the second example embodiment of an inventive system depicted in FIG. 2 can also compensate for an unwanted loading or enriching respectively of the blood mass flow with carbon dioxide ($CO_2$) resulting from adding a CO2-loaded substitute via a fourth inlet 4 prior to the return into the intracorporeal blood circulation of the patient or animal to be treated.

Supplying a more strongly concentrated bloodstream to the adsorber apparatus A potentially increases the clotting risk, in particular in adsorber apparatus A. However, the pressure sensor devices respectively provided immediately ahead of and immediately following each of the three blood treatment apparatus A, D and G can quickly and reliably detect and largely prevent any occurrence of clotting, in particular by additionally adding an anticoagulant into the bloodstream, for example the addition of citrate, via inlet 9 (see FIG. 4). Furthermore, should clotting arise, the respective adsorber apparatus A and/or the respective blood treatment apparatus A, D and/or G affected by the clotting and/or their respective treatment module forming a treatment segment can be replaced.

Figure 3:
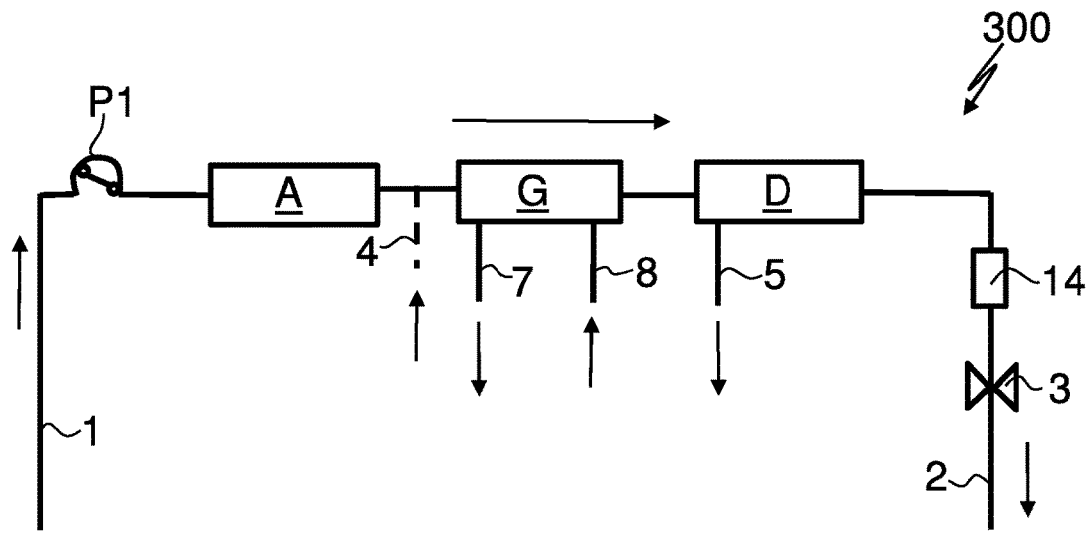

FIG. 3 shows a third example embodiment of an inventive system 300 for extracorporeal blood treatment, wherein this system 300 is of basically similar structure to the two previously described inventive systems 100 and 200, although likewise differs in the order of the arrangement to the individual blood treatment apparatus A, G and D from the two previously described example embodiments of an inventive system 100 and 200 for extracorporeal blood treatment.

In the third example embodiment of an inventive system 300 for treating blood as depicted in FIG. 3, the adsorber apparatus A is, as with the inventive system 100 depicted in FIG. 1, likewise the first to be perfused by the blow mass flow to be treated. However, then the gas exchange apparatus G is thereafter perfused and only then the dialysis apparatus D.

Since the dialysis apparatus D in the example embodiment of an inventive system 300 depicted in FIG. 3 is likewise designed only for hemofiltration and not for hemodialysis, loading of the bloodstream due to an exchange with a CO2-loaded dialysate can no longer occur downstream of the gas exchange apparatus G since the dialysis apparatus is not supplied any dialysate as such is not required for hemofiltration.

The gas exchange apparatus G being arranged downstream of the adsorber apparatus A ensures that a potential unwanted CO2 loading of the bloodstream due to the influx of a CO2-loaded substituate via the fourth inlet 4 can be counterbalanced. By the adsorber apparatus A being arranged downstream of the dialysis apparatus D in the blood flow direction, the dialysis apparatus D can in this case also act as a safety-related filtration stage against unwanted particle intrusion into the adsorber apparatus A arranged upstream in the blood flow. Furthermore, potential unwanted nonspecific additional electrovalences and/or pH shifts occurring in the adsorber apparatus by way of the dialysis apparatus D can also be offset by this arrangement or with this inventive system 300 respectively. Moreover, the hemofilter in the gas exchanger G downstream of the gas exchange apparatus G creates a back pressure which has an advantageous effect on the function of the gas exchanger G.

Figure 4:
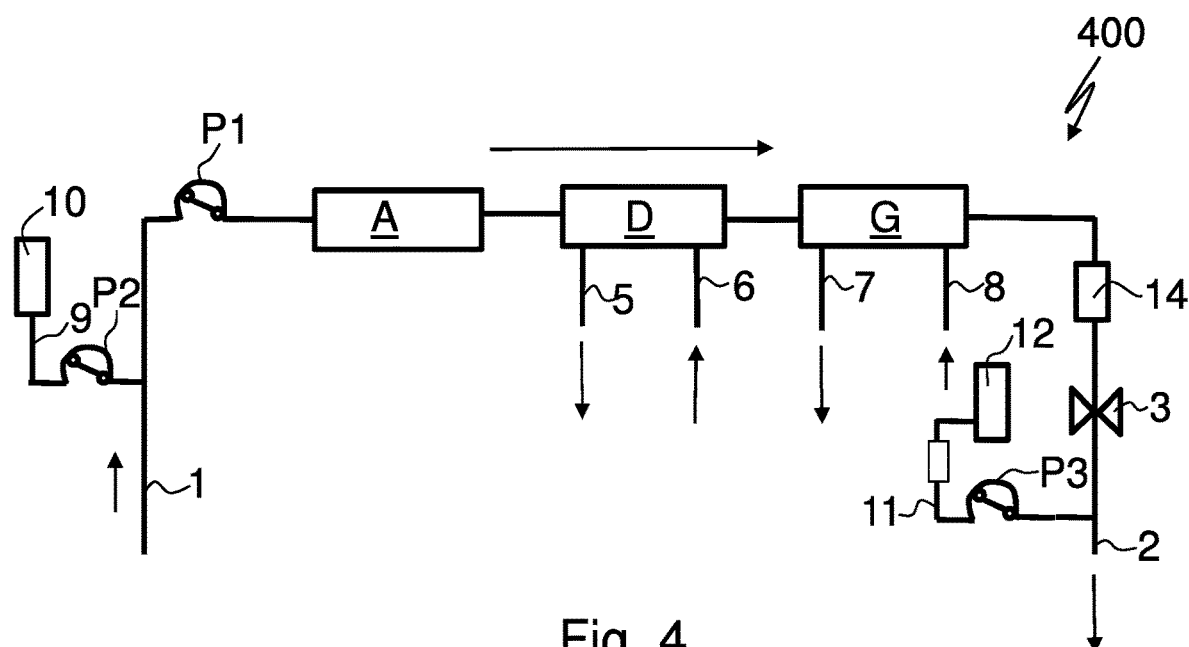

FIG. 4 shows a fourth example embodiment of an inventive system 400 for extracorporeal blood treatment, wherein this embodiment example represents a particularly preferential design of an inventive system for extracorporeal blood treatment and is likewise based on a first example embodiment of an inventive system 100 described on the basis of FIG. 1. Additionally to the inventive system 100 described on the basis of FIG. 1, this system 400 comprises a second inlet 9 as well as a third inlet 11 via which a compound can in each case be supplied to the bloodstream.

A first compound, which is preferably accommodated in a bag 10, can thereby be supplied to the bloodstream to be treated via the second inlet 9 with the aid of a second pump P2, whereby the system 400 in this case is designed such that the first compound can be supplied to the bloodstream immediately after being drawn from the intracorporeal blood circulation of the patient or animal to be treated, in particular prior to the first blood pump P1 in the direction of blood flow and in particular prior to the first blood treatment apparatus perfused by the bloodstream to be treated.

In particular, the system 400 is thereby designed to supply the bloodstream to be treated with a liquid citrate solution as an anticoagulant via the second inlet 9 with the assistance of the second pump P2.

A second compound, in particular a calcium solution to balance the loss of calcium occurring during hemodialysis in the dialysis apparatus D, can be supplied to the system via the third inlet 11 by means of a third pump P3. In this fourth example embodiment of an inventive system 400 for extracorporeal blood treatment depicted in FIG. 4, the second compound is thereby supplied via the third inlet 11 immediately prior to the return of the treated blood to the patient, in particular downstream of check valve 3. It is of course also possible for the third inlet is to be arranged upstream of the check valve 3 in the blood flow direction.

The inventive system 400 depicted in FIG. 4 is thereby particularly suited to extracorporeal blood circulation treatment via veno-venous access; i.e. CVVHD in particular, in which the bloodstream to be treated is drawn from a vein of a patient or animal to be treated and the treated bloodstream returned into a vein.

If the dialysis apparatus D is designed for hemodiafiltration instead of hemodialysis in the inventive system for extracorporeal blood treatment in which the blood treatment apparatus are arranged as described on the basis of FIG. 4, the bloodstream can preferentially be supplied a substitute to balance the fluid loss in the adsorber apparatus A and/or the dialysis apparatus D preferably via an additional inlet 4 after the adsorber apparatus A and ahead of the dialysis apparatus D in the blood flow direction. Alternatively or additionally, the system can also comprise an inlet 4 downstream of the dialysis apparatus D in the blood flow direction for the addition of the substituate to balance out the fluid and/or volume loss in the adsorber apparatus A and/or the dialysis apparatus D. Such a system is particularly suited to post-CVVHDF.

Figure 5:
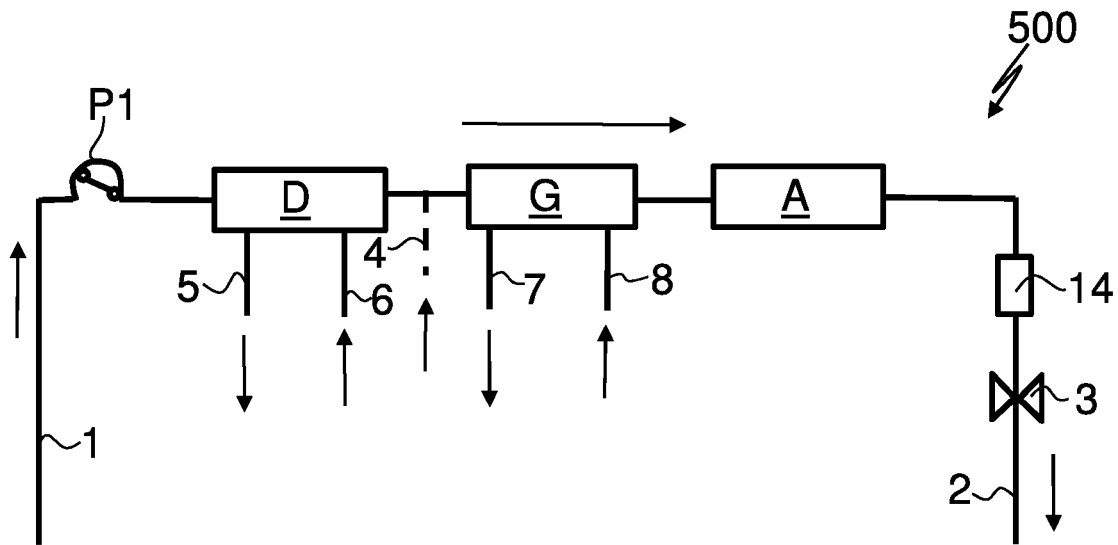

FIG. 5 shows a fifth example embodiment of an inventive system 500 for extracorporeal blood treatment which is likewise based on the inventive system depicted in FIG. 1, albeit differs from the system 100 of FIG. 1 in that the adsorber apparatus A is arranged downstream of the gas exchange apparatus G, in particular downstream of the gas exchange apparatus G and downstream of the dialysis apparatus D. This arrangement has the advantage of the pressure gradient on the gas exchange membrane in the gas exchange apparatus increasing due to the increased back pressure resulting on the adsorber apparatus A, whereby an improved gas exchange can be achieved.

The substituate for compensating the volume loss in the adsorber apparatus A is preferably supplied to the bloodstream via the inlet 4 ahead of the gas exchange apparatus G as is illustrated in FIG. 5. Alternatively or additionally, supply upstream of the dialysis apparatus D is also advantageously feasible. An unwanted $CO_2$ loading by the substituate can thereby be balanced by means of the downstream-arranged gas exchange apparatus G.

Figure 6:
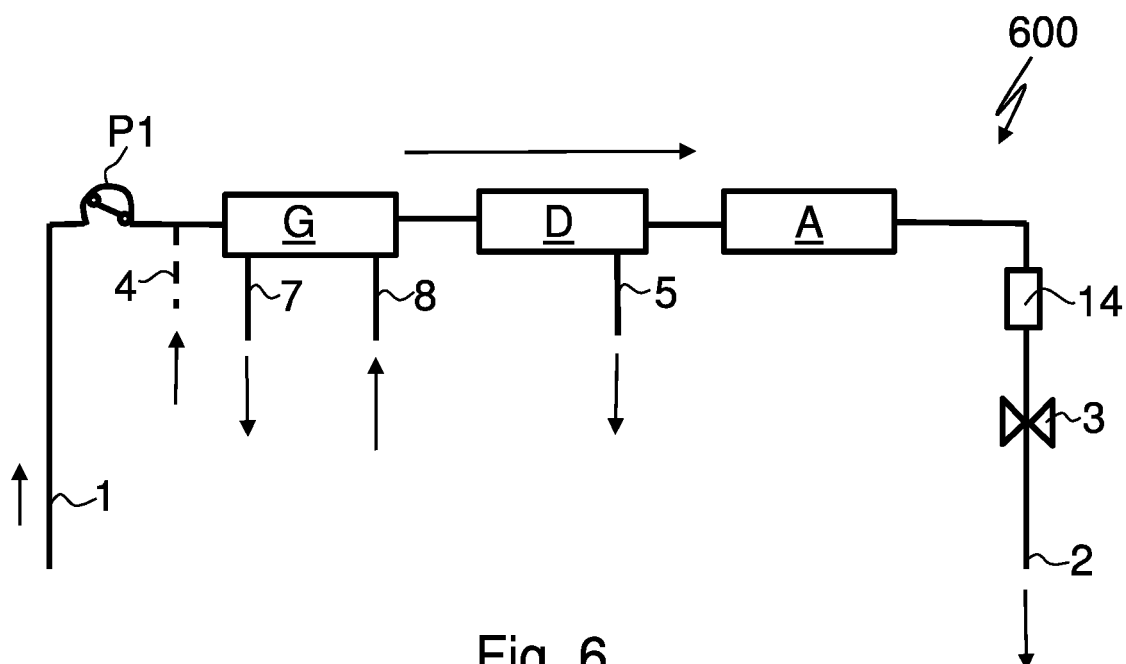

FIG. 6 shows a sixth example embodiment of an inventive system 600 for extracorporeal blood treatment which is based on the inventive system 500 depicted in FIG. 5, albeit differs from the system 500 from FIG. 5 in that the gas exchange apparatus G is in this case arranged upstream of the dialysis apparatus D which, in this case, is only designed for hemofiltration and not for hemodialysis.

This arrangement has the advantage of the back pressure upstream of the dialysis apparatus D and upstream of the adsorber apparatus A in each case acting increasingly on the pressure gradient within the gas exchange device G on the gas exchange membrane, whereby the efficiency of the gas exchange can be increased.

Preferably, the substituate is likewise added to the bloodstream to offset the volume loss in the adsorber apparatus A via the inlet 4 upstream of the gas exchange apparatus G so that unwanted $CO_2$ loading by the substituate can be offset by the downstream-arranged gas exchange apparatus G.

Because the dialysis apparatus D is designed for hemofiltration, which does not require dialysate, unwanted $CO_2$ loading by the dialysate can be avoided.

Figure 7:
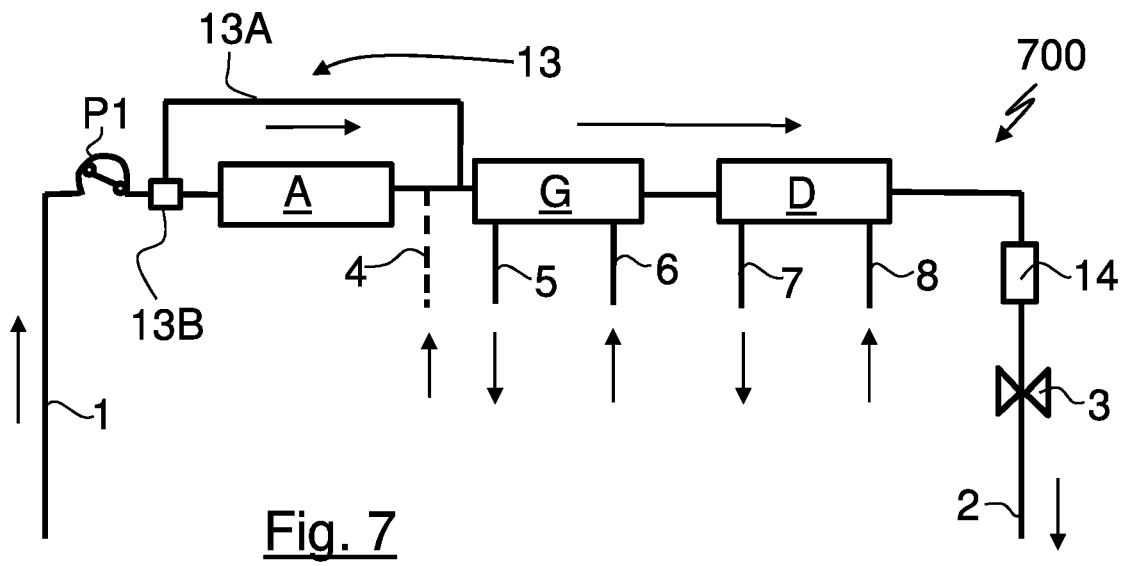

FIG. 7 shows a seventh example embodiment of an inventive system 700 for extracorporeal blood treatment which is likewise based on the inventive system 100 depicted in FIG. 1, however in which a bypass device 13 having a bypass line 13A as well as a bypass valve 13B is additionally provided, same enabling the bloodstream to be treated to bypass the adsorber apparatus A. This system 700 has the advantage of alternatingly enabling a blood treatment with or without adsorption treatment. This thereby considerably increases flexibility in terms of possible applications of an inventive system since adsorption treatment is not indicated in all blood treatment cases or a clotted or almost fully loaded, respectively saturated adsorber can be circumvented.

The bypass valve 13B is thereby preferably designed such that a bloodstream to be treated is respectively either routed entirely through the adsorber apparatus downstream of the bypass valve 13B in the direction of blood flow or entirely bypasses the adsorber apparatus A via the bypass line 13A.

In a particularly advantageous design of a system according to the invention, the system comprises a correspondingly designed bypass line for each of the blood treatment apparatus A, D, G so that an adsorption treatment and/or a gas exchange and/or a dialysis treatment is alternatingly possible with the inventive system.

Figure 8:
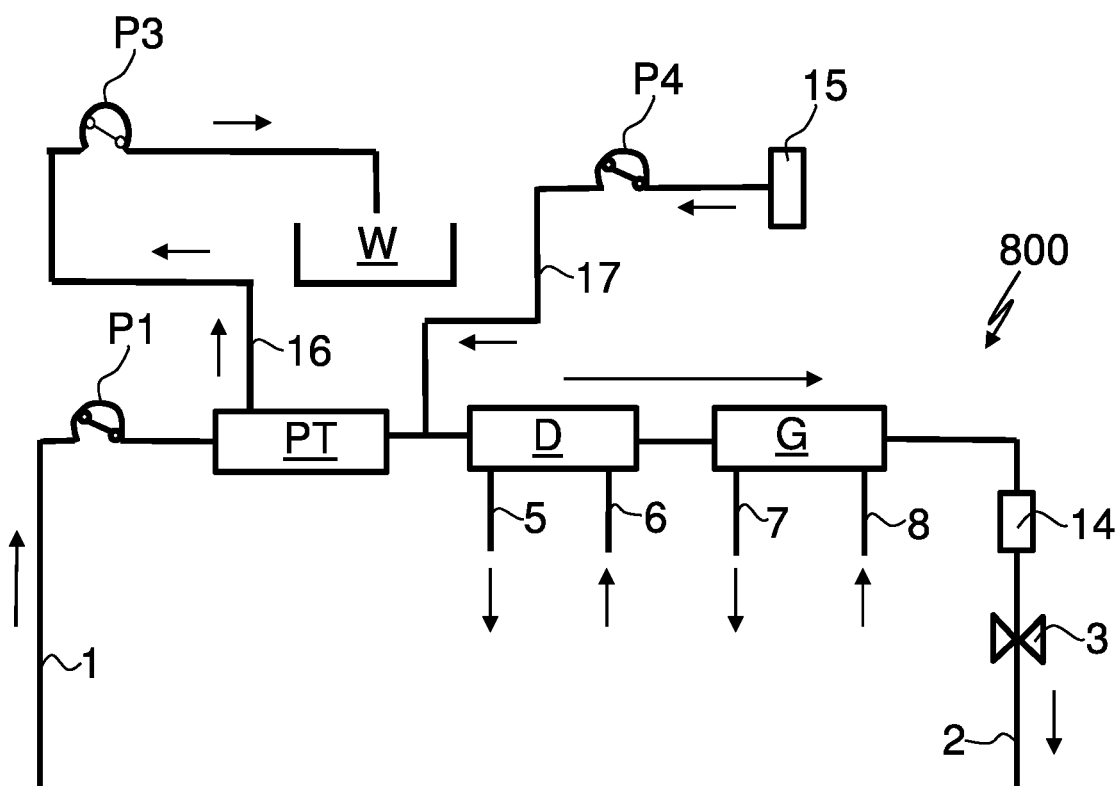

FIG. 8 shows an eighth example embodiment of an inventive system 800 based on the FIG. 1 system 100, wherein instead of an adsorber apparatus A, the first blood treatment apparatus in this example embodiment is a plasma separator apparatus PT in the form of a plasma filter PT, by means of which separated blood plasma can be supplied with the aid of a further, in particular third, pump P3 to a blood plasma disposal container W via a line 16 which forms a fourth outlet for removing separated blood plasma.

To replace the amount of blood plasma removed, the bloodstream can be supplied with fresh plasma via line 17, which forms a seventh inlet 17, particularly by means of a further, in particular fourth, pump P4.

Figure 9:
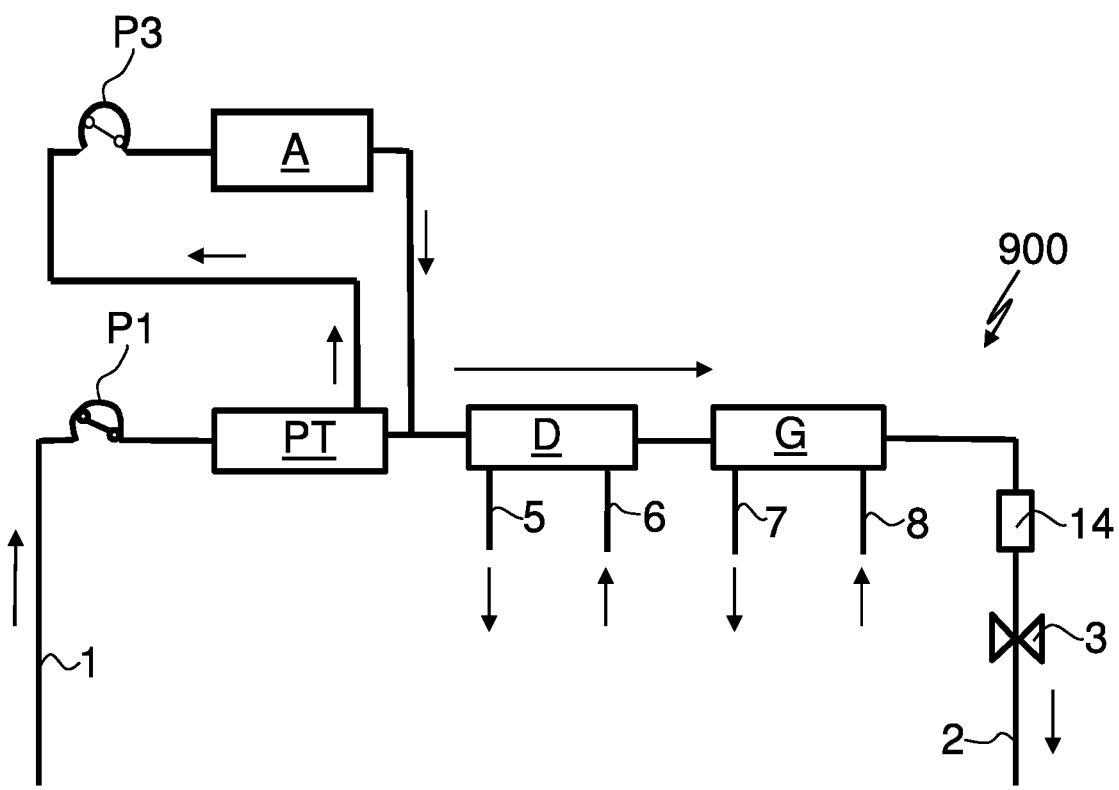

FIG. 9 shows a ninth example embodiment of an inventive system 900 based on the system 800 of FIG. 8, wherein in this example embodiment, the separated plasma is not supplied to a blood plasma disposal container W but rather conducted through a blood treatment apparatus in the form of an adsorber apparatus A by means of a tube line, in particular via a bypass line, wherein the treated plasma is supplied back into the remaining bloodstream after the adsorption treatment, in particular in the main line.

Figure 10:
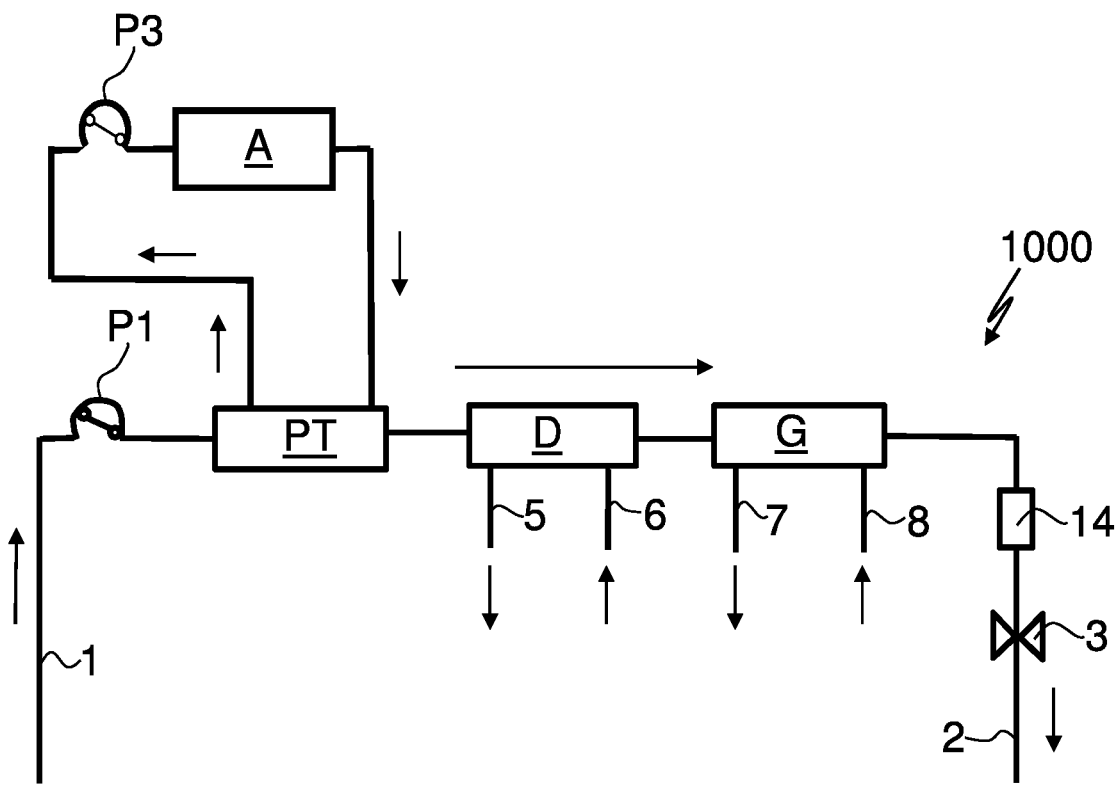

FIG. 10 shows a tenth example embodiment of an inventive system 1000 based on the system 900 of FIG. 9, wherein the separated plasma is not supplied to the remaining bloodstream after the adsorption treatment in this example embodiment but rather to the plasma separator apparatus PT for recirculation in a bypass circuit. Doing so can thereby achieve improved plasma separation and/or adsorption treatment.

LIST OF REFERENCE NUMERALS 100, 200, 300, 400, 500, 600, 700, 800, 900, 1000 inventive system for extracorporeal blood treatment
1 upply line (first inlet)
2 return line (first outlet)
3 check valve
4 fourth inlet for supplying a substituate into the bloodstream
5 second outlet for removing an effluent from the dialysis apparatus
6 fifth inlet for supplying a dialysate into the dialysis apparatus
7 third outlet for removing CO2 from the gas exchange apparatus
8 sixth inlet for supplying a gas or gas mixture into the gas exchange apparatus
9 second inlet for supplying a first compound into the bloodstream
10 bag, filled with a first compound
11 third inlet for supplying a second compound into the bloodstream
12 bag, filled with a second compound
13 bypass device
13A bypass line
13B bypass valve
14 gas bubble detection device
15 bag, filled with fresh blood plasma
16 fourth outlet for removal of separated blood plasma
17 seventh inlet for supplying fresh blood plasma
A adsorber apparatus
D dialysis apparatus
G gas exchange apparatus
PT plasma separator apparatus
P1 first pump, blood pump
P2 second pump
P3 third pump
P4 fourth pump
P5 fifth pump
W blood plasma disposal container

The invention claimed is:

1. A system for extracorporeal blood treatment, wherein the system comprises:
a first inlet configured to introduce a bloodstream to be treated, into the system,
a first blood treatment apparatus configured to receive the bloodstream to be treated and form a first-treated bloodstream,
a second blood treatment apparatus configured to receive the first-treated bloodstream and form a second-treated bloodstream,
a third blood treatment apparatus configured to receive the second-treated bloodstream and form a third-treated bloodstream, and
a first outlet configured to discharge the third-treated bloodstream from the system,
wherein the first blood treatment apparatus is or comprises (a) an adsorber configured to remove at least one exogenous and/or at least one endogenous pathogen, (b) a plasma separator apparatus for separating blood plasma from the other blood components, or (a) and (b),
wherein the second blood treatment apparatus is designed as a dialysis apparatus, and
wherein the third blood treatment apparatus is designed as (c) a gas exchange apparatus, (d) a gas supply apparatus for supplying a gas or gas mixture into a stream of blood flowing through the third blood treatment apparatus, or both (c) and (d), and
wherein the first, second, and third blood treatment apparatuses are sequentially connected, in series, in a functional state of system application between the first inlet and the first outlet of the system relative to a direction of blood flow of a bloodstream to be treated, and are configured to be consecutively perfused extracorporeally by the bloodstream to be treated, the first-treated bloodstream, and the second-treated bloodstream, respectively.

2. The system according to claim 1, wherein the first blood treatment apparatus is or comprises an adsorber apparatus designed for endotoxin adsorption, cytokine adsorption and/or immunoadsorption, wherein the adsorber apparatus is designed to remove at least one pharmaceutical and/or medical drug and/or at least one phytotoxin and/or at least one organic toxin and/or at least one other toxic substance and/or to remove bacteria, viruses, fungi and/or other organisms and/or at least one immune complex and/or at least one immunoglobulin and/or at least one inflammatory response substance of the body and/or antibodies and/or at least one pathogen-associated molecular pattern and/or at least one alarmin.

3. The system according to claim 1, wherein the system comprises at least one first pump, for pumping at least a portion of a bloodstream to be treated, wherein the at least one first pump is arranged between the first inlet in the blood flow direction and the first blood treatment apparatus in the blood flow direction, and is designed to pump the bloodstream to be treated, the first-treated bloodstream, the second-treated bloodstream, and the third-treated bloodstream.

4. The system according to claim 3, wherein the system comprises a further inlet for the addition of a first compound into the bloodstream, wherein the further inlet is arranged in the direction of blood flow such that the compound can be fed into the bloodstream upstream of the at least one first pump and/or upstream of the first blood treatment apparatus.

5. The system according to claim 1, wherein the system comprises a further inlet for the addition of a second compound into the bloodstream wherein the further inlet is arranged in the direction of blood flow such that the compound is capable of being fed into the bloodstream downstream of the dialysis apparatus.

6. The system according to claim 1, wherein the adsorber apparatus and/or the plasma separator apparatus is/are arranged upstream of the gas exchange apparatus in the blood flow direction.

7. The system according to claim 1, wherein the adsorber apparatus and/or the plasma separator apparatus is an adsorber apparatus.

8. The system according to claim 1, wherein the adsorber apparatus and/or the plasma separator apparatus is/are arranged upstream of the dialysis apparatus in the blood flow direction, wherein the dialysis apparatus is designed for hemodialysis.

9. The system according to claim 1, wherein the adsorber apparatus and/or the plasma separator apparatus is a plasma separator apparatus.

10. The system according to claim 1, wherein the dialysis apparatus is arranged upstream of the gas exchange apparatus in the blood flow direction.

11. The system according to claim 1, wherein the dialysis apparatus is designed for hemofiltration and comprises a hemofilter.

12. The system according to claim 1, wherein the system comprises at least one pressure sensor device for determining a bloodstream flow pressure at a defined point in the system, wherein at least one pressure sensor device is arranged directly ahead of and/or directly after at least one treatment segment of a blood treatment apparatus in the blood flow direction.

13. The system according to claim 1, wherein the system comprises at least one gas bubble detection device for detecting a gas bubble in the bloodstream.

14. The system according to claim 1, wherein a treatment segment for at least one blood treatment apparatus is at least partially formed by an exchangeable treatment module.

15. The system according to claim 1, wherein the system comprises at least one switchable bypass device for bypassing at least one blood treatment apparatus.

16. The system according to claim 1, wherein at least one component of the system has a biocompatible and functional coating on a surface coming into contact with the bloodstream to be treated, the first-treated bloodstream, or the second-treated bloodstream.

17. A method for operating a system for extracorporeal blood treatment designed in accordance with claim 1, comprising:
providing a volume of blood to be treated,
introducing a bloodstream to be treated, comprising the volume of blood to be treated, into the system via the first inlet,
perfusing the first blood treatment apparatus with the bloodstream to be treated, to form a first-treated bloodstream,
then perfusing the second blood treatment apparatus with the first-treated bloodstream, to form a second-treated bloodstream,
then perfusing the third blood treatment apparatus with the second-treated bloodstream, to form a third-treated bloodstream, and
discharging the third-treated bloodstream out of the system via the first outlet.

18. The method according to claim 17, wherein the volume of blood to be treated is provided in a first receptacle, and the third-treated bloodstream is discharged into a second receptacle.

19. A method for extracorporeal blood treatment with a system for extracorporeal blood treatment designed in accordance with claim 1, comprising:
incorporating the system for extracorporeal blood treatment into an intracorporeal blood circulation system of a human or animal to be treated, and establishing an extracorporeal blood circuit by connecting the first inlet of the system for extracorporeal blood treatment to a first blood vessel of the human or animal to be treated and connecting the first outlet of the system for extracorporeal blood treatment to a first blood vessel and/or to a second blood vessel of the human or animal,
withdrawing a bloodstream to be treated from the intracorporeal blood circulation system of the human or animal and introducing a bloodstream to be treated into the system for extracorporeal blood treatment via the first inlet of the system for extracorporeal blood treatment,
perfusing the first blood treatment apparatus with the bloodstream to be treated, to form a first-treated bloodstream,
then perfusing the second blood treatment apparatus with the first-treated bloodstream, to form a second-treated bloodstream,
then perfusing the third blood treatment apparatus with the second-treated bloodstream, to form a third-treated bloodstream,
discharging the third-treated bloodstream via the first outlet of the system, and
returning the third-treated bloodstream into the intracorporeal blood circulation system of the human or animal.

20. A treatment apparatus for extracorporeal blood treatment, wherein the treatment apparatus comprises a system designed in accordance with claim 1, wherein the first, the second and the third blood treatment apparatuses of the system are arranged in a common housing and/or accommodated by a common base.

21. A kit for making a system for extracorporeal blood treatment, wherein, as components, the kit comprises at least:
a first blood treatment apparatus configured to receive a bloodstream to be treated and form a first-treated bloodstream,
a second blood treatment apparatus configured to receive the first-treated bloodstream and form a second-treated bloodstream,
a third blood treatment apparatus configured to receive the second-treated bloodstream and form a third-treated bloodstream,
a tubing set having a first inlet for introducing a bloodstream to be treated and a first outlet for discharging a third-treated bloodstream via one or more tubes,
connections enabling the first blood treatment apparatus, the second blood treatment apparatus, and the third blood treatment apparatus to be sequentially connected, in series, between the first inlet and the first outlet of the system relative to a direction of blood flow of a bloodstream to be treated, and
an installation and/or operating guide,
wherein the first blood treatment apparatus is or comprises (a) an adsorber apparatus for removing at least one exogenous and/or at least one endogenous pathogen, (b) a plasma separator apparatus for separating blood plasma from the remaining blood components, or (a) and (b),
wherein the second blood treatment apparatus is designed as a dialysis apparatus, and
wherein the third blood treatment apparatus is designed as (c) a gas exchange apparatus, (d) a gas supply apparatus for supplying a gas or gas mixture into a bloodstream flowing through the third blood treatment apparatus, or (c) and (d), and
wherein the components of the kit are configured to be combined into a system for extracorporeal blood treatment.

* * * * *